(12) United States Patent
Thormar et al.

(10) Patent No.: US 6,596,763 B1
(45) Date of Patent: Jul. 22, 2003

(54) TOPICAL FORMULATIONS CONTAINING AS A THERAPEUTIC ACTIVE AGENT FATTY ACIDS OR FATTY ALCOHOLS OR MONOGLYCERIDE DERIVATIVES THEREOF FOR TREATING OF MUCOSA INFECTIONS

(75) Inventors: Halldor Thormar, Reykjavik (IS); Thordis Kristmundsdottir, Seltjarnarnes (IS)

(73) Assignee: Lipomedica ehf., Reykjavik (IS)

( * ) Notice: Subject to any disclaimer, the term of this patent is extended or adjusted under 35 U.S.C. 154(b) by 0 days.

(21) Appl. No.: 09/297,921

(22) PCT Filed: Nov. 14, 1997

(86) PCT No.: PCT/DK97/00524

§ 371 (c)(1),
(2), (4) Date: Dec. 16, 1999

(87) PCT Pub. No.: WO98/20872

PCT Pub. Date: May 22, 1998

(30) Foreign Application Priority Data

Nov. 14, 1996 (IS) ..................................................... 4386

(51) Int. Cl.⁷ ........................ A61K 31/21; A61K 31/20; A61K 31/045
(52) U.S. Cl. ...................... 514/506; 514/513; 514/558; 514/560; 514/724; 514/739
(58) Field of Search ................................ 514/456, 506, 514/513, 515, 558, 560, 724, 739

(56) References Cited

U.S. PATENT DOCUMENTS

| 5,208,257 A | 5/1993 | Kabara |
| 5,342,625 A | 8/1994 | Hauer et al. |
| 5,434,182 A * | 7/1995 | Isaacs et al. ................ 514/546 |

FOREIGN PATENT DOCUMENTS

| EP | 0 068 552 | 1/1983 |
| EP | 0 105 448 | 4/1984 |
| EP | 0105488 | * 4/1984 |
| EP | 0 483 835 | 5/1992 |
| WO | WO94/15614 | 7/1994 |
| WO | 96/02244 | 2/1996 |
| WO | 98/11887 | 3/1998 |

OTHER PUBLICATIONS

Isaacs et al., *Annals of the New York Academy of Sciences*, vol. 724, pp. 457–464 (1994).

* cited by examiner

*Primary Examiner*—Alton N. Pryor
(74) *Attorney, Agent, or Firm*—Wenderoth, Lind & Ponack, L.L.P.

(57) ABSTRACT

The present invention relates to a method for counteracting infections caused by bacteria, fungi or virus such as Herpes Simplex Virus in skin or mucosal membranes, in particular genital membranes, of a mammal. The method comprises topically administering to the skin or mucosal membrane an effective amount of a formulation comprising a) at least one microbicidal lipid, b) at least one solubilizing agent which keeps the lipid dissolved in the formulation, and optionally 3) a gel-forming agent. The formulation used in the method may suitable be in the form of a hydrogel. The microbicidal lipid is preferably a $C_{6-18}$ fatty acid, such as, e.g., lauric acid, or a derivative thereof, e.g., a monoglyceride such as capric acid 1-monoglyceride. The solubilizing agent may suitably be a glycofurol such as the commercially-available glycofurol 75. The invention also relates to novel pharmaceutical formulations for use in the method.

96 Claims, 3 Drawing Sheets

Release profile of monocaprin from formulation 2A

Release profile of monocaprin from formulation 1B

Effect of receiver fluid pH on release profile of monocaprin from formulation 1R

TOPICAL FORMULATIONS CONTAINING AS A THERAPEUTIC ACTIVE AGENT FATTY ACIDS OR FATTY ALCOHOLS OR MONOGLYCERIDE DERIVATIVES THEREOF FOR TREATING OF MUCOSA INFECTIONS

FIELD OF THE INVENTION

This application is a 371 of PCT/PK97/00524 filed Nov. 14, 1997.

This invention relates to novel valuable uses of microbicidal lipids, in particular to a method for counteracting infection of the genital mucosa of a mammal by virus, pathogenic bacteria or fungi. The invention also relates to novel pharmaceutical formulations which may be used in the method as well as for other valuable uses such as for application to skin or non-genital mucosa.

BACKGROUND OF THE INVENTION

Use of microbicidal compounds in prevention of HIV infection and other sexually transmitted diseases (STD)

The World Health Organization (WHO) has estimated that as of late 1993 15 million adults and children world-wide were infected with HIV and that, in that year, heterosexual transmission accounted for up to 90% of new infections. It is projected that by the year 2000 the cumulative number of HIV infected individuals will reach 30 to 40 million people (Report of a meeting on the development of vaginal microbicides for the prevention of heterosexual transmission of HIV, WHO/GPA/RID/CRD/94.1, Geneva, Switzerland, 1993). Infections are on the rise in the developing countries, particularly in South and Southeast Asia, where the epidemic is to an increasing extent affecting young women of childbearing age. Also in the U.S. and other western societies, heterosexual transmission is causing an increasing proportion of AIDS cases (A. R. Lifson, Preventing HIV: have we lost our way? The Lancet 343, 1306–1307, 1994). These facts emphasise the need for effective means of protection against heterosexual transmission of HIV.

Three types of preventive methods can be used: i) a physical barrier provided by e.g. a condom, ii) a chemical barrier provided by an intravaginal microbicide, and iii) an immunological barrier provided by mucosal immunity resulting from a prophylactic vaccine (C. J. Elias and L. L. Heise, Challenges for the development of female-controlled vaginal microbicides. AIDS 8,1–9,1994).

Since HIV vaccines giving mucosal protection are probably many years away and condoms, although highly effective in preventing HIV infection, have failed to become generally accepted by males in many parts of the world, protective means are required which are under the control of the woman and can, if necessary, be used without the knowledge or consent of the male partner. Vaginal microbicides would meet this requirement and could not only protect the female's reproductive tract against infectious agents in the semen, but could vice versa protect the male's genital mucosa against possible infectious agents in the female's vaginal secretions.

Three types of vaginal microbicides have been considered: i) the microbicides which kill free viruses and virus-infected cells on contact before they can infect the mucosal epithelial cells or lymphocytes and monocytes/macrophages in the mucosa, ii) compounds which prevent infection of mucosal cells by free or cell-associated virus. These include polyanionic polysaccharides and related compounds which are inhibitors of virus adsorption but do not kill virus or virus-infected cells at inhibitory concentrations, and iii) compounds which inhibit replication of virus in infected cells and thus stop the infection locally. Such compounds include, for example, reverse transcriptase inhibitors. The two latter types of compounds are non-contraceptive, i.e. they do not kill sperm cells and are therefore advantageous for women who desire conception but require protection against HIV infection. They are generally water-soluble and supposedly have low toxicity for mucosal membranes. On the other hand, they do not have the broad antimicrobial activity of the membrane-disruptive microbicides, many of which kill a variety of agents causing STD in addition to being spermicidal. A number of products which have been licensed and used as vaginal spermicides have been shown in vitro to have a broad activity against sexually transmitted pathogens including HIV. They include for example nonoxynol-9, octoxynol-9, benzalkonium chloride and menfegol which are used in the form of foams, jellies, creams, sponges, foaming tablets, suppositories, and as coating for condoms. (M. J. Rosenberg, K. K. Holmes et al. Virucides in prevention of HIV infection, Sex. Trans. Dis. 20, 41–44, 1993). In addition to their in vitro activities there is some evidence of in vivo efficacy against gonococcal and clamydial infections (W. C. Louv, et al. A clinical trial of nonoxynol-9 for preventing gonococcal and clamydial infections. J. Infect. Dis. 158, 518–523, 1988). The microbicidal activity of nonoxynol-9 has been studied both in vitro and in vivo. However, the results of clinical trials have been controversial (L. Zekeng et al. Barrier contraceptive use and HIV infection among high-risk women in Cameroon. AIDS 7, 725–731, 1993), but when used frequently or at a high dose nonoxynol-9 may cause vaginal and cervical lesions which could increase the risk of HIV transmission.

Accordingly, there is a need for new products which can be used frequently without adverse effects.

A microbicidal compound should fulfil a number of criteria to qualify as a safe and effective measure for prevention of sexually transmitted HIV infection. Since evidence suggests that HIV-infected lymphocytes and macrophages are the primary infectious elements in semen (D. J. Anderson, Mechanisms of HIV-1 transmission via semen. J. NIH Res. 4, 104, 1992; D. M. Philips and A. S. Bourinbaiar, Mechanism of HIV spread from lymphocytes to epithelia. Virology 186, 261–273, 1992), the compound should efficiently kill these cells in addition to killing free virus in the semen. Preferably, it should also kill other agents transmitting STD, since lesions in the genital mucosa caused by these agents may promote HIV transmission. It should not cause ulcers or other lesions in the genital mucosa and it should not adversely affect the vaginal environment, such as the vaginal flora and pH. Preferably, it should be stable and inexpensive.

Microbicidal Lipids

There are several published reports on antiviral and antibacterial activities of milk lipids (J. K. Welsh et al. Use of Semliki Forest virus to identify lipid-mediated antiviral activity and anti-alphavirus immunoglobulin A in human milk, Infect. Immun. 19, 395–401, 1978; J. K. Welsh et al. Effect of antiviral lipids, heat and freezing on the activity of viruses in human milk, J. Infect. Dis. 140,322–328,1979; J. J. Kabara, Fatty acids and derivatives as antimicrobial agents. In: The pharmacological effect of lipids. Edited by J. J. Kabara. The American Oil Chemists Society, St.Louis, Mo., 1978, pp. 1–13; C. E. Isaacs, H. Thormar et al., Membrane disruptive effect of human milk: Inactivation of enveloped viruses, J. Infect. Dis. 154, 966–971, 1986; C. E. Isaacs and H. Thormar, Human milk lipids inactivate enveloped viruses. In: Breast feeding, Nutrition, Infection and Infant Growth in Developed and Emerging Countries. Edited by S. A. Atkinson, L. A Hanson, R. K. Chandra. ARTS Biomedical Publ. St. Johns, Newfoundland, Canada. 1990, pp. 161–174; C. E. Isaacs et al., Antiviral and antibacterial lipids in human milk and infant formula feeds, Arch. Dis. Childhood 65, 861–864, 1990; C. E. Isaacs and H. Thormar, The role of milk-derived antimicrobial lipids as antiviral and antibacterial agents. In: Immunology of Milk and the Neonate. Edited by J. Mestecky et al. Plenum Press, 1991, pp. 159–165; C. E. Isaacs et al., Addition of lipases to infant formulas produces antiviral and antibacterial activity, J. Nutr. Biochem. 3, 304–308, 1992; C. E. Isaacs et al. Antimicrobial activity of lipids added to human milk, infant formula, and bovine milk, Nutr. Biochem. 6, 362–366, 1995) where the active lipids are free fatty acids and monoglycerides which are released from triglycerides in the milk by milk lipases or lipases of the gastrointestinal tract.

The virucidal effect of purified lipids has been studied in cell culture media (H. Thormar, C. E. Isaacs et al., Inactivation of enveloped viruses and killing of cells by fatty acids and monoglycerides. Antimicr. Agents Chemother. 31, 27–31, 1987; H. Thormar, C. E. Isaacs et. al., Inactivation of visna virus and other enveloped viruses by free fatty acids and monoglycerides. Ann. N.Y. Acad. Sci. 724, 465–471, 1994).

Enveloped viruses, such as herpes simplex virus type 1 (HSV-1), vesicular stomatitis virus (VSV) and visna virus, were found to be inactivated by long-chain unsaturated and medium-chain saturated fatty acids, whereas long-chain saturated and short-chain fatty acids had no or only a very small virucidal effect at the highest concentrations tested. 1-monoglycerides of medium-chain unsaturated fatty acids showed more virucidal activity than the corresponding free fatty acids.

Thus, capric acid 1-monoglyceride (10:0) capric acid 1-monoglyceride is also denoted monocaprin or MC in the following) and lauric acid 1-monoglyceride (12:0) were 10-fold more active than capric and lauric acids (by the designation (X:Y) is meant that a fatty moiety consists of X carbon atoms and comprises Y double bonds). Capric acid 1-monoglyceride at a concentration of 2 mM and lauric acid 1-monoglyceride at a concentration of 1 mM caused a 3000-fold to 10,000-fold reduction in titer of HSV-1, VSV and visna virus when incubated in cell culture medium at 37° C. for 30 min. Diglycerides of fatty acids showed no virucidal activity. An electron microscope study, using the negative staining technique showed that virucidal fatty acids caused leakage of the viral envelope of VSV and at a higher concentration a complete disintegration of the envelope and the viral particles. They also caused disintegration of the plasma membranes of tissue culture cells resulting in cell lysis and death (H. Thormar et al. Antimicrob. Agents Chemother. 31, 27–31, 1987). The mechanism of disruption of cellular and viral membranes by lipids is not known.

Ethers of 6-, 7-, and 8-carbon atom saturated fatty acids were found to be active against visna virus, and the 8-carbon monoglyceride ether 1-0-Octyl-SN-glycerol in a concentration of 25 mM inactivated human immunodeficiency viruses 1 and 2 (HIV-1 and HIV-2) in human plasma by more than $10^9$-fold in 30 min. (C. E. Isaacs, K. S. Kim, and H. Thormar, Inactivation of enveloped viruses in bodily fluids by purified lipids, Ann. N.Y. Acad. Sci. 724, 457–464, 1994). The same study also showed that the lipid concentrations required for viral inactivation in human blood were as much as 10-fold higher than needed for comparable viral inactivation in cell culture medium. Medium-chain monoglycerides had much greater virucidal activity in human blood than long-chain unsaturated monoglycerides, although they were equally active in culture medium. This was attributed to a stronger binding of long-chain fatty acids to plasma proteins and to less solubility.

The microbicidal and cytocidal activities of lipids and their potential applications for killing microorganisms in bodily fluids are described in the U.S. Pat. Nos. 4,997,851 and 5,434,182. Their application for disinfecting contact lenses is described in U.S. Pat. No. 5,624,958.

SUMMARY OF THE INVENTION

According to the present invention, it has been found that suitable microbicidal lipids may be formulated in such a way that they are capable of killing virus and bacteria so surprisingly fast and efficiently in environments prevailing at genital mucosal membranes such as the vaginal mucosa that the formulations can realistically be used for the prevention of sexually transmitted diseases.

The particular formulation or composition (in the present context, these terms are synonymous) contains the microbicidal lipid dissolved in the formulation by means of a solubilizing agent allowing the lipid to exert its killing effect in the aqueous environment prevailing at genital mucosal membranes such as the vaginal mucosa.

Thus, one aspect of the present invention relates to a method for counteracting infection of the genital mucosa of a mammal, including a human, by virus, pathogenic bacteria or fungi, comprising topically administering, to the genital mucosa of the mammal, an effective amount of a formulation which contains a) at least one microbicidal lipid as an active ingredient, and b) at least one solubilizing agent which keeps the lipid dissolved in the formulation.

Another aspect of the invention relates to novel pharmaceutical formulations which contain a) at least one microbicidal lipid as an active ingredient, and b) at least one solubilizing agent which keeps the lipid dissolved in the formulation.

A further aspect of the invention relates to a method for preventing or treating infections caused by virus, bacteria or fungi in skin or mucosal membranes, in particular oral or anal mucosal membranes and/or skin adjacent thereto, comprising topically administering an effective amount of a formulation which contains a) at least one microbicidal lipid as an active ingredient, and b) at least one solubilizing agent which keeps the lipid dissolved in the formulation, the formulation being, in particular, a novel formulation according to the invention.

DETAILED DESCRIPTION OF THE INVENTION

The term "microbicidal lipid" is used herein to designate a lipid which is capable of killing viruses and/or bacteria. As explained above, such lipids have been known for some time, and have been found also to have cytocidal effect. Killing of a virus means that the virus, upon effective exposure to the lipid, will be unable to infect cells, i.e. the virus will be unable to introduce its genetic material into a cell wherein the genetic material can be reproduced. Killing of a bacterium or a cell means that the bacterium or the cell, upon effective exposure to the lipid, is no longer capable of performing the basic functions of life; particularly, the bacterium or the cell will no longer be able to obtain the necessary nutrition in order to maintain the physical integrity of the cell. As is seen from the claims and explanations given herein, it is contemplated, and considered justified to assume, that the lipids also analogously have a potent fungicidal effect.

In the following, the term "microbicidal lipid" also covers lipids having cytocidal effect so that the term is, for these lipids, synonymous with "microbicidal and cytocidal lipid". The cytocidal effect means that the lipids can kill leukocytes in sperm, which is a highly desired effect. The microbicidal lipids will also decrease the motility and viability of sperm cells and thus have a contraceptive effect.

The term "counteract infection" means preventing infection or stopping the further development of an infection which has already taken place, such as by inhibiting replication of, or killing, e.g. bacteria or viruses in infected cells. Thus, the method can be performed as a therapeutic method for treatment of already infected genital mucosas. However, the main importance of the method is presently seen in the fast and immediate action of the microbicidal lipid or lipids in prevention of infection in connection with sexual intercourse, or stopping the further development of an infection which is taking place, both of which actions depend on the surprising and exceptional fastness with which the microbicidal lipids, when solubilized in the formulation, can exert their activity in the very specific environment prevailing at the genital mucosa in the use of the formulation, in particular in connection with sexual intercourse.

It is preferred that the formulation is applied to the vaginal mucosa at the most 1 hour before sexual intercourse, preferably at the most 45 minutes before sexual intercourse, such as at the most 30 minutes before sexual intercourse, still more preferably at the most 15 minutes before sexual intercourse, e.g. at the most 10 minutes before sexual intercourse, in particular at the most 5 minutes before sexual intercourse, such as immediately before sexual intercourse. The formulation may also be applied to the vaginal mucosa at the beginning of the sexual intercourse, e.g. by coating the outside of a condom with the formulation.

The presently preferred formulation comprises a gel or gel-like composition, in particular a hydrogel, which will be discussed in greater detail in the following, but it is contemplated that also other formulations which can be applied to and remain in contact with genital mucosas, and in which the solubilizing agent can keep the lipid in solution in a manner which is compatible or miscible with the mucosal environment, in particular an aqueous solution, may also be useful.

The aqueous solution in the formulation is preferably provided by having water as a constituent, normally a major constituent, of the formulation, but it is contemplated that the aqueous solution may also in certain cases be provided by the formulation attracting, in situ, water from the mucosal environment, although such formulations which do not contain water as an initial constituent are presently not preferred.

Examples of such other formulations (that is, formulations which do not comprise gels or gel-like compositions), are liquids or pastes of sufficient viscosity, typically a dynamic viscosity above the dynamic viscosity of water, spray formulations, e.g. based on such liquids or pastes, foam formulations, including expanding foam formulations, e.g. delivered from an aerosol product. Common to all these formulations is that they contain the lipid or lipids dissolved, by means of the solubilizing agent, in a propellant or a mixture of solvent and propellant, or dissolved in the solubilizing agent itself. It is believed to be an important feature of any such composition that the composition is capable of being applied to and remain for a relevant period of time on the genital mucosa in question and for at least an initial part of the period during which it remains on the genital mucosa to enable contact between the lipid in dissolved form and the mucosal environment.

A particularly suitable formulation for use in the method is a gel formulation, in particular a hydrogel. A detailed discussion of hydrogels is found in Knuth et al. (K. Knuth, M. Amiji and J. R. Robinson, Hydrogel delivery systems for vaginal and oral applications. Advanced Drug Delivery Reviews, 11, 137–167, 1993). Hydrogels are established using hydrophilic natural or synthetic polymers that have the ability to swell in an aqueous environment without any substantial dissolution. Examples of suitable polymers (or "water gelling agents") for use in establishing a hydrogel for use in the method of the invention are water gelling agents selected from the group consisting of polysaccharides, such as, e.g., cellulose derivatives which are hydroxypropyl cellulose, hydroxypropyl methylcellulose, hydroxyethyl methylcellulose and carboxymethylcellulose and salts thereof; acrylic polymers such as polyacrylic acids and polymethacrylates, e.g. carbopol, poly(hydroxyethyl methacrylate), poly(methoxyethyl methacrylate) and poly(methoxyethoxyethyl methacrylate); proteins such as gelatine; high average molecular weight polyhydroxy compounds such as polyvinyl alcohols; high average molecular weight polyalkylene glycols such as polyethylene glycols, optionally cross-linked, with an average molecular weight from about 20,000 to about 4,000,000; and polyvinylpyrrolidone with an average molecular weight in the range from 10,000 to 700,000.

As more specific suitable examples of such water gelling agents can be mentioned carbomer such as Carbopol 934, Carbopol 940 and Carbopol 941, povidone K29–32, such as povidone K30, carboxymethylcellulose and salts thereof, hydroxypropylmethylcellulose, and polycarbophil.

Especially interesting water gelling agents may also show bioadhesive properties, i.e. the water gelling agent aids in the attachment of the drug carrier system to a specific biological location. Thus, bioadhesion localises drugs in a particular region and thereby improves and enhances the availability of the drug to the localised area.

The bioadhesive properties of various water gelling agents have been studied by Chen et al. (J. L. Chen, G. N. Cyr. Compositions producing adhesion through hydration. In Adhesive. Biological System, Edited by R. S. Manly, Academic Press, New York, 1970, chapter 10), Park et al. (H. Park, J. R Robinson. Mechanism of mucoadhesion of poly(acrylic acid) hydrogels. Pharm. Res. 4, 457–465, 1987), and Kriwet et al. (B. Kriwet, T. Kissel. Interactions between bioadhesive poly(acrylic acid) and calcium ions. Int. J. Pharm. 127, 135–145, 1996) which are hereby incorporated by reference.

The microbicidal lipid is typically a lipid selected from the group consisting of $C_{6-18}$ fatty acids or salts thereof, $C_{6-18}$ fatty acid monoglycerides, $C_{6-18}$ fatty acid esters of monohydric alcohols, $C_{6-18}$ fatty alcohols, and $C_{6-18}$ fatty alcohol monoglyceride ethers, the $C_{6-18}$ chain containing at least one double or triple bond when the number of carbon atoms thereof exceeds 15. Among these, preferred lipids are lipids selected from the group consisting of $C_{6-14}$ fatty acids or salts thereof, $C_{6-14}$ fatty acid monoglycerides, $C_{6-14}$ fatty acid esters of monohydric alcohols, $C_{6-14}$ fatty alcohols, and $C_{6-14}$ fatty alcohol monoglyceride ethers, in particular such lipids in which the fatty moieties are saturated.

In the present context the term "$C_{6-18}$ fatty acids" is intended to mean saturated fatty acids or unsaturated fatty acids comprising one or more double bonds, having a total number of carbon atoms of from 6 to 18. In a similar way, the term "$C_{6-14}$ fatty acids" is intended to mean saturated fatty acids or unsaturated fatty acids comprising one or more double bonds, having a total number of carbon atoms of from 6 to 14, preferably saturated fatty acids having a total number of carbon atoms of from 6 to 14.

Specific examples of suitable saturated $C_{6-18}$ is fatty acids are e.g. caproic acid (6:0), enanthic acid (7:0), caprylic acid (8:0), pelargonic acid (9:0), capric acid (10:0), undecylenic acid (11:0), lauric acid (12:0), tridecylic acid (13:0), myristic acid (14:0) palmitic acid (16:0), and stearic acid (18:0), and salts and mixtures thereof.

Specific examples of suitable unsaturated $C_{6-18}$ is fatty acids comprising one or more double bonds are e.g. palmitoleic acid (16:1), oleic acid (18:1), elaidic acid (18:1), linoleic acid (18:2), and linolenic acid (18:3), and salts and mixtures thereof.

Specific examples of suitable saturated $C_{6-14}$ fatty acids are e.g. caproic acid (6:0), enanthic acid (7:0), caprylic acid (8:0), pelargonic acid (9:0), capric acid (10:0), undecylenic acid (11:0), lauric acid (12:0), tridecylic acid (13:0), and myristic acid (14:0), and salts and mixtures thereof.

In the present context, the term "$C_{6-18}$ fatty acid monoglycerides" is intended to mean monoglycerides of $C_{6-18}$ fatty acids, wherein the ester bond is established between the acid moiety of the $C_{6-18}$ fatty acid and one of the primary alcohol groups of glycerol. In a similar way, the term "$C_{6-14}$ fatty acid monoglycerides" is intended to mean monoglycerides of $C_{6-14}$ fatty acids, preferably saturated fatty acids, having a total number of carbon atoms of from 6 to 14.

Specific examples of suitable $C_{6-18}$ fatty acid monoglycerides are e.g. caproic acid 1-monoglyceride, caprylic acid 1-monoglyceride, pelargonic acid 1-monoglyceride, capric acid 1-monoglyceride, undecylenic acid 1-monoglyceride, lauric acid 1-monoglyceride, myristic acid 1-monoglyceride, palmitic acid 1-monoglyceride, stearic acid 1-monoglyceride, palmitoleic acid 1-monoglyceride, oleic acid 1-monoglyceride, elaidic acid 1-monoglceride, linoleic acid 1-monoglyceride, and linolenic acid 1-monoglyceride, and mixtures thereof.

Specific examples of suitable $C_{6-14}$ fatty acid monoglycerides are e.g. caproic acid 1-monoglyceride, caprylic acid 1-monoglyceride, pelargonic acid 1-monoglyceride, capric acid 1-monoglyceride, undecylenic acid 1-monoglyceride, lauric acid 1-monoglyceride, and myristic acid 1-monoglyceride, and mixtures thereof.

In the present context the term "monohydric alcohol" is intended to mean alcohols with from 1 to 12 carbon atoms, preferably from 1 to 6 carbon atoms, which may be straight, branched or cyclic, and may contain one or more double and/or triple bonds, such as methyl alcohol, ethyl alcohol, n-propyl alcohol, iso-propyl alcohol, n-butyl alcohol, iso-butyl alcohol, sec-butyl alcohol, tert-butyl alcohol, n-pentyl alcohol, iso-pentyl alcohol, n-hexyl alcohol, n-octyl alcohol, n-dodecyl alcohol, n-dodecyl alcohol, cyclopentyl alcohol, cyclohexyl alcohol, allyl alcohol, and crotyl alcohol.

Accordingly, the term "$C_{6-18}$ fatty acid esters of monohydric alcohols" is intended to mean esters wherein the $C_{6-18}$ fatty acid moiety and the monohydric alcohol moiety are as defined above. In a similar way, the term "$C_{6-14}$ fatty acid esters of monohydric alcohols" is intended to mean esters wherein the $C_{6-14}$ fatty acid moiety and the monohydric alcohol moiety are as defined above.

Specific examples of suitable $C_{6-18}$ fatty acid esters of monohydric alcohols are e.g. caproic acid methyl ester, caprylic acid methyl ester, capric acid methyl ester, undecylenic acid methyl ester, lauric acid methyl ester, myristic acid methyl ester, palmitic acid methyl ester, stearic acid methyl ester, palmitoleic acid methyl ester, oleic acid methyl ester, elaidic acid methyl ester, linoleic acid methyl ester, linolenic acid methyl ester, caproic acid ethyl ester, caprylic acid ethyl ester, capric acid ethyl ester, undecylenic acid ethyl ester, lauric acid ethyl ester, myristic acid ethyl ester, palmitic acid ethyl ester, stearic acid ethyl ester, palmitoleic acid ethyl ester, oleic acid ethyl ester, elaidic acid ethyl ester, linoleic acid ethyl ester, linolenic acid ethyl ester, caproic acid n-propyl ester, caprylic acid n-propyl ester, capric acid n-propyl ester, undecylenic acid n-propyl ester, lauric acid n-propyl ester, myristic acid n-propyl ester, palmitic acid n-propyl ester, stearic acid n-propyl ester, palmitoleic acid n-propyl ester, oleic acid n-propyl ester, elaidic acid n-propyl ester, linoleic acid n-propyl ester, linolenic acid n-propyl ester, caproic acid iso-propyl ester, caprylic acid iso-propyl ester, capric acid iso-propyl ester, undecylenic acid iso-propyl ester, lauric acid iso-propyl ester, myristic acid iso-propyl ester, palmitic acid iso-propyl ester, stearic acid iso-propyl ester, palmitoleic acid iso-propyl ester, oleic acid iso-propyl ester, eaidic acid iso-propyl ester, linoleic acid iso-propyl ester, and linolenic acid iso-propyl ester, and mixtures thereof.

In the present context the term "$C_{6-18}$ fatty alcohols" is intended to mean saturated monohydric alcohols or unsaturated monohydric alcohols comprising one or more double bonds, having a total number of carbon atoms of from 6 to 18. In a similar way, the term "$C_{6-14}$ fatty alcohols" is intended to mean monohydric alcohols, preferably saturated monohydric alcohols, having a total number of carbon atoms of from 6 to 14.

Specific examples of suitable $C_{6-18}$ fatty alcohols are e.g. n-hexyl alcohol (6:0), n-heptyl alcohol (7:0), n-octyl alcohol (8:0), n-nonyl alcohol (9:0), n-dodecyl alcohol (10:0), n-undecyl alcohol (11:0), n-dodecyl alcohol (12:0), n-tridecyl alcohol (13:0), n-tetradecyl alcohol (14:0), n-pentadecyl alcohol (15:0), n-hexadecyl alcohol (16:0), n-heptadecyl alcohol (17:0), n-octadecyl alcohol (18:0), and mixtures thereof.

Specific examples of suitable $C_{6-14}$ fatty alcohols are e.g. n-hexyl alcohol (6:0), n-heptyl alcohol (7:0), n-octyl alcohol (8:0), n-nonyl alcohol (9:0), n-dodecyl alcohol (10:0), n-undecyl alcohol (11:0), n-dodecyl alcohol (12:0), n-tridecyl alcohol (13:0), n-tetradecyl alcohol (14:0), palmitoleyl alcohol (16:1), oleyl alcohol (18:1), elaidyl alcohol (18:1), linoleyl alcohol (18:2), and linolenyl alcohol (18:3), and mixtures thereof.

In the present context the term "$C_{1-18}$ fatty alcohol monoglyceride ethers" is intended to mean ethers, wherein the ether bond is established between the $C_{6-18}$ fatty hydrocarbon moiety of the $C_{6-18}$ alcohol and one of the primary alcohol groups of glycerol. In a similar way term "$C_{6-14}$ fatty alcohol monoglyceride ethers" is intended to mean ethers, wherein the ether bond is established between the $C_{6-14}$ fatty hydrocarbon moiety, preferably a saturated $C_{6-14}$ fatty hydrocarbon moiety, of the $C_{6-14}$ alcohol and one of the primary alcohol groups of glycerol.

Specific examples of suitable "$C_{6-18}$ fatty alcohol monoglyceride ethers" are e.g. 1-caproyl-glycerol ether, 1-enanthyl-glycerol ether, 1-caprylyl-glycerol ether, 1-pelargonyl-glycerol ether, 1-capryl-glycerol ether, 1-undecylenyl-glycerol ether, 1-lauryl-glycerol ether, 1-tridecylyl-glycerol ether, 1-myristyl-glycerol ether, 1-palmityl-glycerol ether, 1-stearyl-glycerol ether, 1-palmitoleyl-glycerol ether, 1-oleyl-glycerol ether, 1-elaidyl-glycerol ether, 1-linoleyl-glycerol ether, and 1-linolenyl-glycerol ether, and mixtures thereof.

Specific examples of suitable "$C_{6-14}$ fatty alcohol monoglyceride ethers" are e.g. 1-caproyl-glycerol ether, 1-enanthyl-glycerol ether, 1-caprylyl-glycerol ether, 1-pelargonyl-glycerol ether, 1-capryl-glycerol ether, 1-undecylenyl-glycerol ether, 1-lauryl-glycerol ether, 1-tridecylyl-glycerol ether, and 1-myristyl-glycerol ether, and mixtures thereof.

There can be a considerable variation between the rates or degrees of the microbicidal properties of the individual lipids of the above classes of lipids in connection with the method of the invention. However, the present inventors have provided suitable assays enabling the person skilled in the art to select effective and preferred lipids based on such assays which can be performed as simple preliminary tests. Examples of these or similar assays are given in the experimental section of the present description.

Thus, Example 1 discloses a simple test for the inherent activity of a lipid with respect to inactivating virus (exemplified by HSV-1 and VV virus) within the extremely short time of 1 minute, as well as results of the test, and Example 10 discloses a simple test for the inherent activity of a lipid with respect to inactivating C. trachomatis within 10 minutes. Using these tests, the inherent suitability of a lipid or a mixture of lipids for use in the method of the invention can be initially assessed, the rationale being that if a lipid does not show a significant effect in at least one of these test, it is normally not carried further in any testing.

The requirement to formulations suitable for the demanding purpose of the present invention is that on the one hand, the lipid or lipid mixture should be brought in contact, in dissolved state obtained by means of the solubilizing agent in the particular formulation, with the genital mucosal environment, and on the other hand, the formulation itself should incur a minimum of loss of the inherent activity of the lipid or lipid mixture.

On this basis, assays have been developed which give an assessment of the capability of a formulation to exert the microbicidal activity of the lipid or lipid mixture contained in solubilized form in the formulation. Such assays, as well as the results thereof, are illustrated in Example 3 (HSV-1 virus), Example 6 (HIV-1 virus) and Example 11 (C. trachomatis). These types of assays are excellent preliminary tests which can be easily performed by the person skilled in the art to assess the suitability of any given formulation constructed in accordance with the principles disclosed herein.

Based on this, formulations suitable for use in the method of the invention are formulations which,
  when incubated for 5 minutes with HSV-1 in a titer of 100 million $CCID_{50}$ per ml in Cell Culture Maintenance Medium in a concentration corresponding to 5 millimolar lipid, will cause at least a thousand fold reduction of the virus titer, preferably at least a ten thousand fold reduction and more preferably at least a hundred thousand fold reduction, or which,
  when incubated for 1 minute with HIV-1 in a titer of 10 million $CCID_{50}$ per ml in Cell Culture Maintenance Medium in a concentration corresponding to 20 millimolar lipid will cause at least a hundred fold reduction of the virus titer, preferably at least a thousand fold reduction and more preferably at least a ten thousand fold reduction, or which,
  when incubated for 10 minutes with C. trachomatis in a titer of 10 million IFU per ml in Cell Culture Maintenance Medium in a concentration corresponding to 5 millimolar lipid will cause at least a thousand fold reduction of the bacterial titer, preferably at least a ten thousand fold reduction and more preferably at least a hundred thousand fold reduction.

Evidently, it is preferred that a formulation fulfils two or preferably all three of the above criteria on at least the stated lowest level, more preferably on the stated intermediate level and most preferably on the stated highest level.

Based on experiments of the above types carried out so far, it is presently preferred that the lipid is selected from capric acid 1-monoglyceride, lauric acid, palmitoleic acid, and mixtures thereof, as these have shown very high microbicidal activities. The presently most preferred lipid is capric acid 1-monoglyceride.

Furthermore, the formulation should be stable on the conditions prevailing at the site of application, i.e. it is of outmost importance that the active lipid does not leak out of the formulation since, as discussed above, the lipid or lipid mixture should be brought in contact with the genital mucosal environment in a dissolved state. The present inventors have developed assays suitable for an initial assessment of the stability of such formulations used in the method of the invention. The results of such assays (or drug release curves) are shown in FIGS. 1, 2 and 3. Based on such in vitro release curves, which can be easily carried out by a person skilled in the art, the stability of a given formulation can be initially assessed. Thus, a preferred formulation for use in the method of the invention is a formulation which, when subjected to the "Drug release from gels" test as defined in the Material and Methods section herein, releases at the most 50% of the active lipid within 1 hour, preferably at the most 45%, still more preferably at the most 40%, such as at the most 35%, in particular at the most 30%, e.g. at the most 25%.

The solubilizing agent should be one which is able to keep the lipid in the effective concentration in solution in the formulation, that is, the formulation should be clear to the naked eye at room temperature or at any rate at the temperature prevalent at the site of application, normally 37° C. when the formulation is adapted for administration to the genital of a human. At the same time, the solubilizing agent should, of course, be pharmaceutically acceptable and should, like other constituents of the formulation, give rise to as little irritation at the site of application as possible, and preferably substantially no irritation. A suitable assay indicating whether a formulation containing a solubilizing agent gives rise to vaginal mucosal irritation as manifested by macroscopic and microscopic lesions is disclosed in Example 12 herein, together with results for a number of formulations with and without the active lipid. As will be seen, it is possible to devise formulations which give rise to no or substantially no irritation. Evidently, such an assay can be used by the person skilled in the art to perform preliminary assessment of the suitability of an individual solubilizing agent and other constituents of a formulation, as well as the formulation as a whole, with respect to minimal irritation.

Suitable classes of solubilizing agents are solubilizing agents selected from lower polyhydric alcohols such as e.g. glycerol, ethylene glycol, propylene glycol, 1,3-propanediol and pentaerythriol; polyalkylene glycols of low average molecular weight such as e.g. polyethylene glycol 200 to 600; and polyhydroxy ether derivatives such as e.g. glycofurols.

Preferably, the solubilizing agent is constituted by a compound or compounds selected from the group consisting of compounds of the general formula I:

$$R-(O-(CH_2)_n)_m-OH \quad (I)$$

wherein n is an integer in the range from 1 to 4, m is an integer in the range from 1 to 15, and R is H or $R_1CH_2$, wherein $R_1$ designates a 5- or 6-membered aliphatic ring wherein from one to three carbon atoms may be replaced by nitrogen and/or oxygen atoms, said 5- or 6-membered ring optionally carrying from one to three substituents selected from the group consisting of halogen, such as fluoro, chloro, bromo, and iodide, amino, carboxy, and hydroxy;

and the closely related compounds of the general formula II:

$$R-(O-CH_2-CH(CH_3))_k-OH \quad (II)$$

wherein k is an integer in the range from 1 to 15, and

R is H or $R_1CH_2$, wherein $R_1$ is as defined above.

In formulae I and II, one or more hydrogen atoms in the repeating units may optionally be substituted by substituents selected from the groups consisting of amino, hydroxy, and halogen, such as fluoro, chloro, bromo and iodide.

The solubilizing agent may, of course, also be a mixture of a compound or compounds of the general formula I and a compound or compounds of the general formula II.

Considering solubilizing agents of the general formula I, n is preferably 2 or 3, more preferably n is 2, i.e. in a preferred embodiment of the method of the invention formula I has the general structure

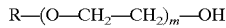
$$R-(O-CH_2-CH_2)_m-OH$$

wherein m is an integer in the range from 1–15, preferably in the range from 1–8, such as from 1–4, and still more preferably m is 1 and/or 2.

Preferably R is H or $R_2CH_2$, wherein $R_2$ designates a 5- or 6-membered aliphatic ring wherein from one to three carbon atoms may be replaced by nitrogen and/or oxygen atoms. More preferably R is H or $R_3CH_2$, wherein $R_3$ designates a 5- or 6-membered ring, preferably a 5-membered ring, wherein one or two, preferably one, carbon atom(s) may be replaced by (an) oxygen atom(s).

Thus, specific examples of interesting solubilizing agents of the general formula I are e.g. compounds selected from the group consisting of monoethylene glycol, diethylene glycol, triethylene glycol, tetraethylene glycol, pentaethylene glycol, hexaethylene glycol, heptaethylene glycol, octaethylene glycol, nonaethylene glycol, decaethylene glycol, undecaethylene glycol, dodecaethylene glycol, tridecaethylene glycol, tetradecaethylene glycol, and pentadecaethylene glycol, and mixtures thereof. The ethylene glycols may be used in the form of a single compound or a mixture of two or more ethylene glycols, e.g. commercial available products such as polyethylene glycol 200 (PEG 200), polyethylene glycol 300 (PEG 300), polyethylene glycol 400 (PEG 400), polyethylene glycol 500 (PEG 500), and polyethylene glycol 600 (PEG 600), and any mixture thereof.

Also very interesting examples of solubilizing agents of the general formula I are solubilizing agents selected from the group consisting of glycofurols of the general formula III

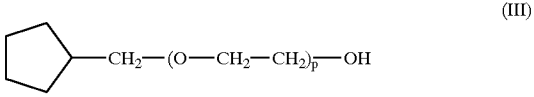
$$\text{(III)}$$
$$-CH_2-(O-CH_2-CH_2)_p-OH$$

wherein p is an integer in the range from 1 to 15, preferably in the range from 1 to 8, such as from 1 to 4, and more preferably p is 1 and/or 2.

Thus, specific examples of interesting solubilizing agents of the general formula III are e.g. compounds selected from the group consisting of mono glycofurol (corresponds to n=1 in formula III), di glycofurol (corresponds to n=2 in formula III), tri glycofurol, tetra glycofurol, penta glycofurol, hexa glycofurol, hepta glycofurol, octa glycofurol, nona glycofurol, deca glycofurol, undeca glycofurol, dodeca glycofurol, trideca glycofurol, tetradeca glycofurol, and pentadeca glycofurol, and mixtures thereof.

As will be understood from the examples provided herein a particular suitable solubilizing agent of the general formula III is Glycofurol 75 which refers to commercially available solubilizing agents of the above formula III, wherein p is mainly 1 and 2 (i.e. a mixture of mainly mono- and di glycofurol). (Chemical Abstract Registration No. [9004 76-6]).

Furthermore, any mixture of glycofurols of the general formula III, preferably glycofurol 75, and one or more of the above-mentioned ethylene glycols are very interesting solubilizing agents with respect to the method of the present invention.

Considering solubilizing agents of the general formula II, R is preferably H or $R_2CH_2$, wherein $R_2$ is as defined above. More preferably R is H or $R_3CH_2$, wherein $R_3$ is as defined above. In particular interesting embodiments of the method according to the invention R is preferably H, i.e. in a preferred embodiment of the method of the invention formula II has the general structure

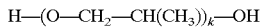
$$H-(O-CH_2-CH(CH_3))_k-OH$$

wherein k is an integer in the range from 1 to 15, preferably in the range from 1 to 8, still more preferably in the range from 1 to 4.

Thus, specific examples of interesting solubilizing agents of the general formula II are e.g. compounds selected from the group consisting of monopropylene glycol, dipropylene glycol, tripropylene glycol, tetrapropylene glycol, pentapropylene glycol, hexapropylene glycol, heptapropylene glycol, octapropylene glycol, nonapropylene glycol, decapropylene glycol, undecapropylene glycol, dodecapropylene glycol, tridecapropylene glycol, tetradecapropylene glycol, and pentadecapropylene glycol, and mixtures thereof, preferably monopropylene glycol, dipropylene glycol, tripropylene glycol, tetrapropylene glycol, pentapropylene glycol, hexapropylene glycol, heptapropylene glycol, and octapropylene glycol, and mixtures thereof, and still more preferably monopropylene glycol, dipropylene glycol, tripropylene glycol, and tetrapropylene glycol, and mixtures thereof.

As will be evident from the examples provided herein, monopropylene glycol (or "propylene glycol") is not preferred as the sole solubilizing agent in the formulations used in the method of the invention since propylene glycol used as the sole solubilizing agent caused vaginal mucosal irritation as disclosed in Example 12 herein.

It is envisaged, however, that propylene glycol may be a useful solubilizing agent in the formulations used in the method of the invention when used in combination with other solubilizing agents of the general formulae I or II. Thus, it is envisaged that a preferred mixture comprising propylene glycol, is a mixture of propylene glycol and glycofurols of the general formula III, preferably glycofurol 75, wherein the propylene glycol is present in an amount from 0.1 to 99% by weight, calculated on the total amount of solubilizing agent, preferably the propylene glycol is present in an amount from 0.1 to 90% by weight, such as from 0.1 to 75% by weight, still more preferably from 0.1 to 50% by weight, e.g. such as from 0.1 to 40% by weight, in particular from 0.1 to 30% by weight, such as from 0.1 to 20% by weight, calculated on the total amount of solubilizing agent.

As mentioned above the presently most preferred solubilizing agent is glycofurol 75. Although, at the molecular level, it is not clear why glycofurol is superior to e.g. propylene glycol with respect to toxicology, it is envisaged that a solubilizing agent, or a mixture of solubilizing agents, with an average molecular weight that resemble that of glycofurol 75 may be very interesting solubilizing agents for the purpose of the method of the invention. Thus, preferred solubilizing agents are solubilzing agents selected from the group consisting of monoethylene glycol, diethylene glycol, triethylene glycol, tetraethylene glycol, monopropylene glycol, dipropylene glycol, tripropylene glycol, and tetrapropylene glycol, and mixtures thereof.

In the formulations used in the method of the present invention, the microbicidal lipid or lipids is/are present in the formulation in a total concentration of about 1 to 40 millimolar, preferably in a concentration of about 5 to 30 millimolar, still more preferably in a concentration of about 10 to 25 millimolar, in particular in a concentration of about 15 to 23 millimolar, such as in a concentration of about 20 millimolar.

As will be evident from the examples provided herein, the amount of solubilizing agent can be varied within a broad range. It is, however, a requirement that the amount of solubilizing agent is present in such a concentration that the formulation, at room temperature, is substantially clear to the naked eye.

Subject to this, the solubilizing agent is preferably present in a concentration in the range of 5–95% by weight, based on the formulation, such as e.g. 5–90% by weight, e.g., 5–80% by weight, such as 10–60% by weight, more often 10–50% by weight, e.g., 20–40% by weight, such as e.g. around 30% by weight, based on the formulation.

The formulation used in the method of the invention may also comprise additional pharmaceutically acceptable excipients, such as e.g. one or more non-ionic surfactants, one or more preservatives, as well as one or more pH modifiers, provided, of course, that these additional excipients are so selected with respect to their qualitative properties and the amounts in which they are incorporated that they do not to any substantial extent impair the activity of the microbicidal lipid.

Examples of pharmaceutically acceptable non-ionic surfactants include e.g. bile salts and derivatives thereof, fusidic acid and derivatives thereof, and polysorbates, such as Tween 20 to 85, preferably Tween 20, Tween 40, Tween 60, and Tween 80, still more preferably Tween 20 and Tween 40, in particular Tween 20.

The non-ionic surfactant(s) is/are preferably present in the formulation in such a concentration between 0.01 to 2% by weight, calculated on the formulation, that it does not to any substantial extent impair the activity of the lipid or lipids.

Interesting preservatives suitable for the formulation used in the method of the invention are preservatives selected from the group consisting of benzoic acid or derivatives thereof. Preferably the preservatives are selected from the groups consisting of $C_{1-6}$-alkyl-p-hydroxy-benzoic acids, such as methyl-p-hydroxy-benzoic acid, ethyl-p-hydroxy-benzoic acid, propyl-p-hydroxy-benzoic acid, butyl-p-hydroxy-benzoic acid, and mixtures thereof. In a particular interesting embodiment, the preservative is a mixture of methyl-p-hydroxy-benzoic acid and propyl-p-hydroxy-benzoic acid, in the proportion of from about 3:1 to about 5:1 by weight, preferably in the proportion of about 4:1 by weight.

The preservative or preservatives is/are preferably present in the formulation in such a concentration of about 0.05–0.2% by weight calculated on the formulation, that it does not to any substantial extent impair the activity of the lipid or lipids.

In certain embodiments the composition used in the method of the invention also comprises one or more pharmaceutically acceptable pH modifiers in order to adjust the pH of the composition to the desired pH. Any pharmaceutically acceptable pH modifier, which will be known by the person skilled in the art, may be used, e.g. lactic acid, citric acid, nitric acid, phosphoric acid, acetic acid, dibasic sodium phosphate, sodium or potassium hydroxide, etc.

The formulation for use in the method of the invention may further, in addition to the microbicidal lipid or lipids, comprise one or more antiviral agents selected from agents which are also spermicides, and/or agents which counteract adsorption or fusion of virus to cells and/or agents which counteract proliferation of virus in infected cells, and/or the antiviral agent or agents are selected from the group consisting of reverse transcriptase inhibitors, DNA polymerase inhibitors and protease inhibitors.

Examples of suitable agents which are also spermicides are e.g. surfactants such as nonoxynol-9, chelating agents such as ethylenediaminetetraacetic acid (EDTA), channel-forming ionophores such as gramicidin, and other spermicidal agents such as benzalkonium chloride, sodium docusate and cholate acid and salts thereof.

Examples of suitable agents which counteract adsorption of virus to cells are chemokines and polyanionic compounds selected from e.g. sulphated polysaccharides such as dextran sulphate, heparin, and pentosan polysulphate, and other sulphated polymers such as sulphated polyvinyl alcohol (PVAS), and sulphated copolymers such as sulphated copolymers of acrylic acid and vinyl alcohol (PAVAS). Preferably the agent is a chemokine.

The invention also relates to the use of at least one microbicidal lipid and at least one solubilizing agent therefor for the preparation of a formulation which contains a) the at least one microbicidal lipid as an active ingredient, and b) the at least one solubilizing agent which keeps the lipid dissolved in the formulation, the formulation being for use for counteracting infection of the genital mucosa of a mammal, including a human, by virus, pathogenic bacteria or fungi, in particular by topically administering, to the genital mucosa of the mammal, an effective amount of the formulation.

In accordance with the appended patent claims, the invention also relates to a novel pharmaceutical formulation per se. In a still further aspect, the invention relates to a method for preventing and/or treating infections caused by bacteria, fungi or virus in skin or mucosal membranes of a mammal, in particular of a human.

As explained herein, the formulation preferably comprises a hydrogel. It is normally preferred that the hydrogel "phase" with the lipid dissolved therein by means of the solubilizing agent constitutes a major constituent of the formulation, such as at least about 50% by weight of the formulation and more preferred at least 70% by weight, still more preferred at least 90% by weight of the formulation and often most of the hydrogel with the lipid dissolved therein by means of the solubilizing agent constitutes at least 95% by weight of the formulation, any remainder being constituted by, e.g., other active drug substances and/or other pharmaceutically acceptable excipients which may form part of the hydrogel.

Apart from being directly applied on the site at which the formulation shall exert its effect it is also possible to administer the formulation by means of a suitable formed device. Especially, when the application is to the vagina or rectum or to surroundings of the vagina or the rectum suitable devices may be applied such as devices well known in the art for vaginal and/or rectal administration.

As mentioned above, the invention also relates to novel formulations which can be used for the method discussed above, as well as for other valuable uses which will be discussed in the following.

In general, the formulations suitable for use according to the invention comprises a microbicidal lipid and a solubilizing agent. Novel formulations comprising a microbicidal lipid and a solubilizing agent is of course within the scope of the invention. The hitherto only known formulation which may fall under the above-mentioned definition is described in WO 96/02244 as a formulation containing: Oleic acid (4.40% by weight), sodium hydroxide (0.64% by weight), propylene glycol (50.00% by weight), Methocel K-15 (1.90% by weight), purified water (q.s), citric acid 20% solution to pH 7.3–7.5 in gel. This formulation is without the scope of the formulation aspects of the invention.

In other aspects, the novel formulations of the invention can be defined as i) a pharmaceutical formulation comprising a hydrogel which contains a) at least one microbicidal lipid as an active ingredient, b) at least one water gelling agent, and c) at least one solubilizing agent which keeps the lipid dissolved in the hydrogel, ii) a pharmaceutical formulation comprising a) at least one microbicidal lipid as an active ingredient selected from the group consisting of $C_{1-14}$ fatty acids or salts thereof, $C_{6-14}$ fatty acid monoglycerides, $C_{6-14}$ fatty acid esters of monohydric alcohols, $C_{6-14}$ fatty alcohols, $C_{6-14}$ fatty alcohol monoglyceride ethers, unsaturated $C_{16}$ fatty acids or salts thereof, unsaturated $C_{16}$ fatty acid monoglycerides, unsaturated $C_{16}$ fatty acid esters of monohydric alcohols, unsaturated $C_{16}$ fatty alcohols, and unsaturated $C_{16}$ fatty alcohol monoglyceride ethers and b) a solubilizing agent which keeps the lipid dissolved in the formulation.

In a further aspect the invention relates to a method for preventing or treating infections caused by bacteria, fungi or virus in skin or mucosal membranes, in particular oral or anal mucosal membranes and/or skin adjacent thereto, comprising topically administering an effective amount of a formulation which contains a) at least one microbicidal lipid as an active ingredient, and b) at least one solubilizing agent which keeps the lipid dissolved in the formulation, the solubilizing agent is a compound or compounds selected from the group consisting of compounds of the general formula I:

$$R-(O-(CH_2)_n)_m-OH \qquad (I)$$

wherein n is an integer in the range from 1 to 4, m is an integer in the range from 1 to 15, and R is H or $R_1CH_2$, wherein $R_1$ designates a 5- or 6-membered aliphatic ring wherein from one to three carbon atoms may be replaced by nitrogen and/or oxygen atoms, said 5- or 6-membered ring optionally carrying from one to three substituents selected from the group consisting of halogen, amino, carboxy, and hydroxy;

and compounds of the general formula II:

$$R-(O-CH_2-CH(CH_3))_k-OH \qquad (II)$$

wherein k is an integer in the range from 2 to 15, and

R is H or $R_1CH_2$, wherein $R_1$ is as defined above.

Examples of infections to be treated or prevented by the method according to the invention may be any infection of the skin or mucosa caused by bacteria, virus or fungi towards which the microcidal lipids described herein are effective. Mucosa or mucosal membranes or surfaces may be the oral, aural, nasal, lung, gastrointestinal, vaginal or rectal mucosa (as well as the surroundings) and the skin may be intact skin or skin which in some way have been injured. Examples of such fungi, bacteria and virus which can cause infection of the skin or mucosa are e.g. fungi such as e.g. Dermatophytes, Black piedra, White piedra, *Tines nigra*, and *Tines versicolor*; bacteria such as e.g. *Escherichia coli, Pseudomonas aerginosa*, and *Staphylooccus aureus*; virus such as e.g. influenza virus A, influenza virus B, influenza virus C, parainfluenza virus, mumps virus, Newcastle disease virus, viruses of rinderpest, canine distemper virus, respiratory syncytial virus, rabies virus, herpes simplex type 1, herpes simplex type 2, herpes genitalis, varicella zoster, cytomegalovirus, and Epstein-Barr virus.

It is also contemplated that the lipid is useful for the prevention or treatment of infection by a retrovirus such as e.g. human immuno deficiency Virus (HIV), sarcoma viruses, leukemia viruses, and human lymphotropic viruses types 1 and 2, and/or for the prevention or treatment of acquired immune deficiency syndrome (AIDS).

As will be understood, details and particulars concerning the novel formulation aspects of the invention will be the same as or analogous to the details and particulars of the formulation discussed above in accordance with the method aspect of the invention, and this means that whenever appropriate, the statements concerning the method discussed in detail herein, the formulations for use in the method and improved properties of such formulations apply mutatis mutandis to the novel formulations according to the invention as well as to the other method aspects of the invention.

The invention is further illustrated by the working examples described in the following.

BRIEF DESCRIPTION OF THE DRAWINGS

Relationship between percent capric acid 1-monoglyceride released from the formulation 2A when measured in a membraneless diffusion cell at 37° C., and using an aqueous medium containing 1.0% 2-hydroxypropyl-β-cyclodextrin at pH 4.5 as the receiver phase. FIG. 1 shows that about 40% of the capric acid 1-monoglyceride is released after 1 h, whereas the capric acid 1-monoglyceride has been completely released from the gel formulation after 6 hrs.

Relationship between percent capric acid 1-inonoglyceride released from the formulation 1B when measured in a membraneless diffusion cell at 37° C., and using an aqueous medium containing 1.0% 2-hydroxypropyl-β-cyclodextrin at pH 4.5 as the receiver phase. FIG. 2 shows that about 20% of the capric acid 1-monoglyceride is released after 1 h, and that even after 6 hrs only about 41% of the capric acid 1-monoglyceride has been released from the gel formulation.

Figure 1:
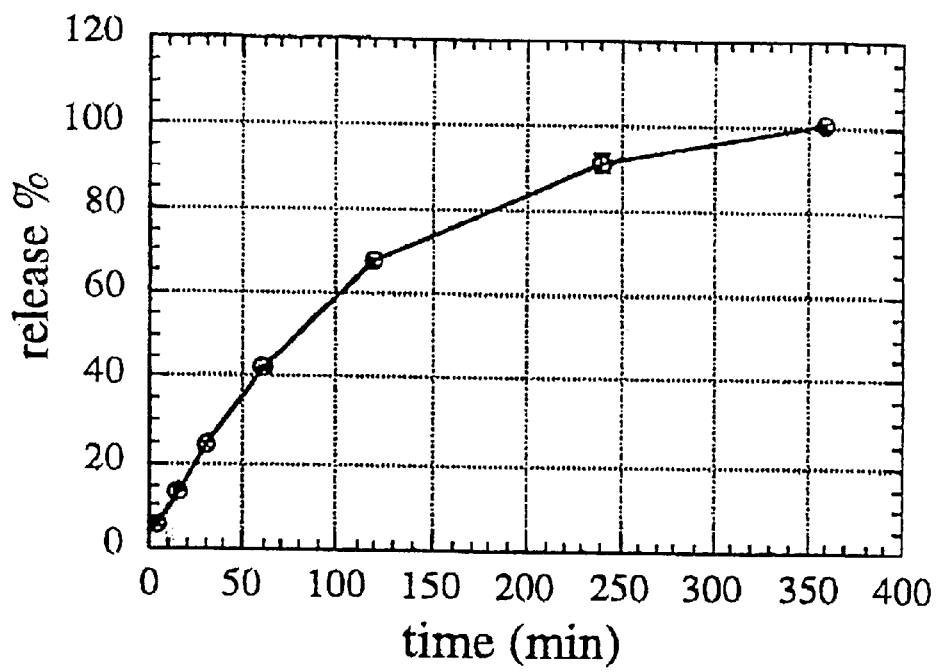
FIG. 1: Release profile of capric acid 1-monoglyceride from formulation 2A

Relationship between percent capric acid 1-monoglyceride released from the formulation 1R when measured in a membraneless diffusion cell at 37° C., and using an aqueous medium containing 1.0% 2-hydroxypropyl-β-cyclodextrin at pH 4.0, 5.0, and 6.0, respectively, as the receiver phase.

LIST OF ABBREVIATIONS

CV-1 cells: African green monkey kidney cell line
C. trachomatis: Chlamydia trachomatis
$CCID_{50}$: 50% cell culture infective dose
CPE: Cytopathic effect
D-MEM: Dulbecco's Modified Eagle Medium
FBS: Fetal bovine serum
FIV: Feline immunodeficiency virus type 1
HSV-1: Herpes simplex virus type 1
2-HPβC: 2-hydroxypropyl-β-cyclodextrin
HPMC: Hydroxypropylmethyl cellulose
HPLC: High performance liquid chromatography
IFU: Inclusion forming units
M: Molar, moles per litre
mM: Millimolar
MM: Maintenance medium (2% FBS in D-MEM)
MC: Monocaprin (capric acid 1-monoglyceride)
NaCMC: Sodium carboxymethylcellulose
STD: Sexually transmitted disease
SCPC: Sheep choroid plexus cells
VW: Visna virus
WBC: White blood cells

EXPERIMENTAL

Materials and Methods

Cell Cultures and Media

CV-1 cells (African green monkey kidney cell line) were grown in Dulbecco's Modified Eagle Medium (D-MEM) with 2 mM L-glutamine, 20 μg/ml of gentamicin and 10% heat-inactivated fetal bovine serum (FBS). Sheep fibroblast cultures were obtained from the choroid plexus of a lamb brain and grown in D-MEM with 20% lamb serum. The maintenance medium (MM) for CV-1 cell monolayers was D-MEM with 2% FBS and for sheep choroid plexus cells (SCPC) D-MEM with 2% lamb serum. MT-4 cells, a T4⁺ lymphocyte cell line, were grown and maintained in RPMI 1640 medium with 10% FBS (J.Balzarini et al., Anti-retrovirus specificity and intracellular metabolism of 2',3'-didehydro-2',3'-dideoxythymidine (d4T, stavudine) and its 5'-monophosphate triester prodrug So324, Molec. Pharmacol. 50, 1207–1213, 1996). McCoy cells were grown in RPMI 1640 medium with 5% FBS. All media were obtained from GIBCO, Paisley, Scotland.

Viruses and Bacteria

Herpes simplex virus type 1 (HSV-1) strain MacIntyre was obtained from the American Type Culture Collection (ATCC), Rockville, Md., USA and grown in monolayers of CV-cells. Visna virus (VV) strain K796 (H. Thormar et al. Antimicr. Agents Chemother. 31, 27–31, 1987) was grown in monolayers of SCPC. Infectious fluids were clarified by centrifugation at 3500 rpm for 10 minutes (Sorvall RT 6000D) before use in experiments. HIV-1 strain $III_B$ (J.Balzarini et al., Molec. Pharmacol. 50, 1207–1213, 1996) was grown and maintained in MT-4 cells. Chlamydia trachomatis (C. trachomatis) was obtained from the ATCC and grown in McCoy cell cultures.

Reagents

Fatty acids and monoglycerides (purest grade) as well as sodium carboxymethylcellulose (NaCMC, high viscosity), tetra glycol (glycofurol 75) and polyvinylpyrrolidone (Av. Mol. Wt. 40000, K: 28–32; Povidon K 29–32) were purchased from Sigma Chemical Co., St. Louis, USA. Carbomer (Carbopol 934) was from Nomeco, Copenhagen, Denmark and hydroxypropylmethylcellulose (HPMC) was purchased from Aldrich Chemical Company Inc., Milwaukee, U.S.A. All other chemical were reagent grade. All other chemicals, i.e. solubilizing agents, pH modifiers, preservatives and non-ionic surfactants, were reagent grade Production of gels Guidelines for producing gel formulations according to the invention are given below. The compositions of all the formulations produced are compiled in Table 1 below.

Formulation Based on Carbopol® 934 and Hydroxypropylmethylcellulose.

| | | |
|---|---|---|
| Hydroxypropylmethylcellulose (HPMC) | 1% | 0.5 g |
| Carbopol ® 934 | 0.5% | 0.25 g |
| Aqua purificata | | ~15 mL |
| Glycofurol 75 | 30% | 15 g |
| Monocaprin | 0/20 mM | 0 g/0.25 g |
| 2% sodium hydroxide solution | | ad pH-5.5 |
| Aqua purificata | | ad g 50 |

HPMC was dispersed in 10 ml of hot (80–90° C.) purified water in a glass beaker. The solution was allowed to cool to about 30–35° C. under continuous stirring at room temperature and then chilled in a refrigerator at about 4° C. for at least one hour. The carbopol® polymer was suspended in 5 ml of purified water at room temperature under vigorous stirring to prevent lumping. It was then mixed with the HPMC solution. Next, the monocaprin, previously dissolved in the glycofurol, was added. Gelling of the carbopol® polymer was induced by raising the pH to approximately 5.5 by dropwise addition of a 2% sodium hydroxide solution. The gel was brought to its final weight (50 g) with purified water. Finally, the gel was centrifuged at high speed (>8000 rpm) for 60 minutes.

Formulation Based on Sodium Carboxymethylcellulose and Povidone K30.

| | | |
|---|---|---|
| Glycofurol 75 | 30% | 15 g |
| Monocaprin | 0/20 mM | 0 g/0.25 g |
| Sodiumcarboxymethylcellulose (NaCMC) | 2% | 1 g |
| Polyvinylpyrrolidone (Povidone) K30 | 1% | 0.5 g |
| 10% lactic acid solution | 1,3% | 0.65 g |
| Aqua purificata | | ad g 50 | monocaprin and Povidone were dissolved individually in the glycofurol in a glass beaker. Following the suspension of NaCMC in the mixture, the lactic acid solution was added dropwise, adjusting the pH of the gel to a value near 5.0, and then purified water, bringing the solution to a final weight of 50 g. Immediately after the addition of water, the solution was stirred continuously until a gel was produced. The gel was centrifuged at high speed (>8000 rpm) for 60 minutes. Finally, the acidity of the gel was measured with a pH-meter.

HPLC Assay of Monocaprin

The monoglyceride content was determined using a high-performance liquid chromatography (HPLC) component system consisting of a Thermo Separations Products Spectra Series P200 HPLC solvent delivery system, a $\mu$Bondapak® C18 125A 10 $\mu$m (3.9×300 mm) column, a Waters Intelligent Sample Processor (WISP™) Model 710B, a Thermo Separations Products SP4400 Intergrator and a Thermo Separations Products Spectra Series UV150 detector. The wavelength was 218 nm and the mobile phase consisted of acetonitrile, water and tetrahydrofuran (57:42:1) with the retention time being 2.1 min at 1.25 ml/min flow rate.

Drug Release From Gels

Figure 2:
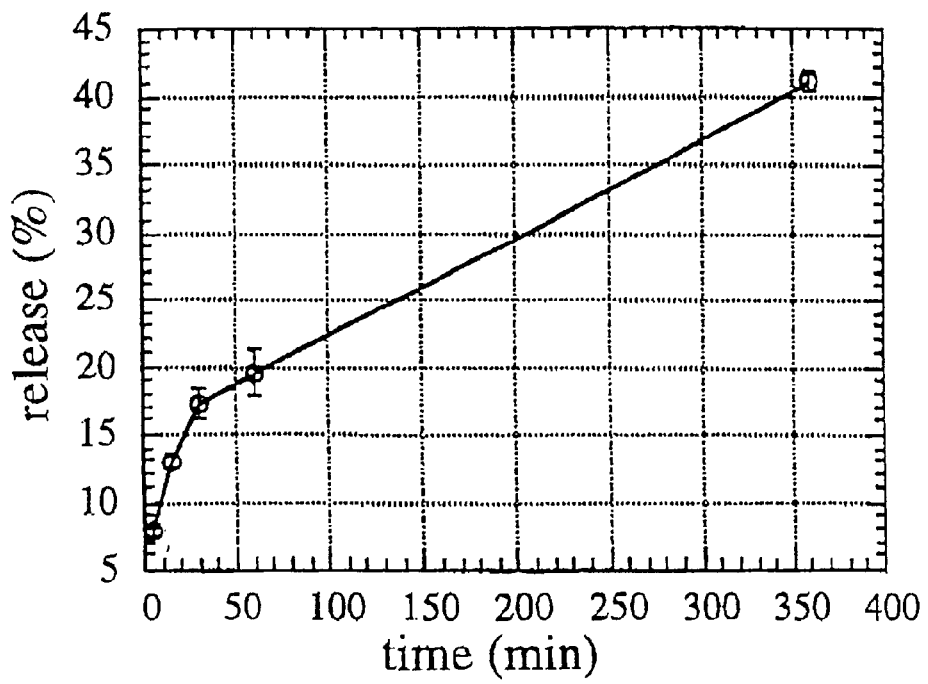
FIG. 2: Release profile of capric acid 1-monoglyceride from formulation 1B
Figure 3:
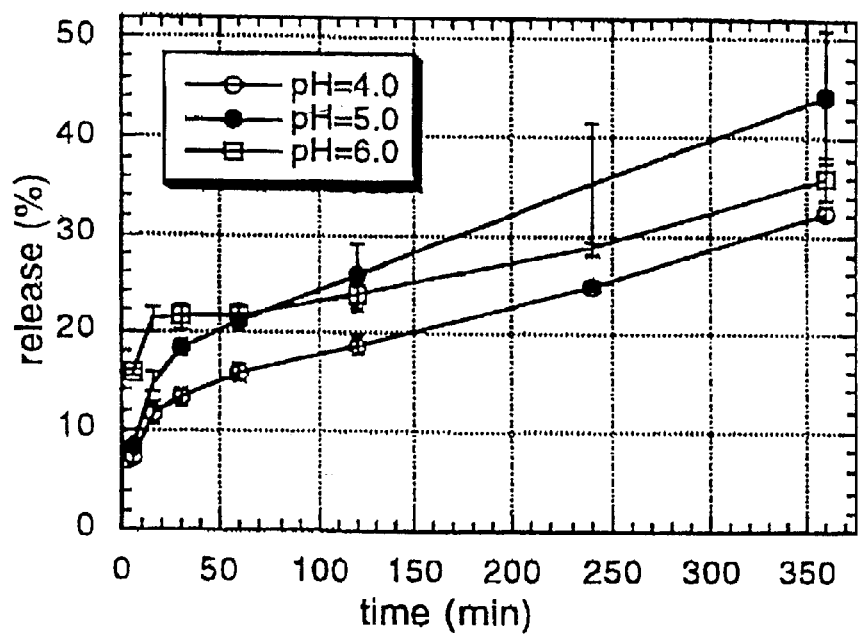
FIG. 3: Release profile of capric acid 1-monoglyceride from formulation 1R at various pH values.

Release of monoglyceride was investigated using a membraneless diffusion cell at 37° C. Phosphate buffer (pH 4.5) containing 0.3% Brij was used as the receiver phase. Samples were taken from the receiver phase at regular intervals and filtered through a 0.22 $\mu$m membrane filter. After each sampling the volume was replaced. The amount of monoglyceride released was determined by HPLC using a calibration curve of the monoglyceride in the receiver phase. Each experiment was carried out in triplicate. The release curves for selected formulations are depicted in FIGS. 1, 2, and 3.

Titration of Virus and Bacteria

HSV-1 and VV were titrated by inoculation of serial 10-fold dilutions in MM into monolayers of CV-1 cells (HSV-1) or SCPC (VV) in 96-well microtiter tissue culture plates (Nunc, Roskilde, Denmark). 100 $\mu$l of virus dilution were inoculated into each well with four wells per dilution. The plates were incubated in a $CO_2$-incubator at 37° C. and were examined for cytopathic effect (CPE) at 3 and 6 days for HSV-1 and at 7 and 14 days for VV. HIV-1 was titrated in serial 5-fold dilutions in 96-well microtiter tissue culture plates (Nunc). The first virus dilution ($10^{-2}$) was pipetted into six wells with 125 $\mu$l per well. The 5-fold serial dilutions were made in the culture plate, and $3 \times 10^4$ MT-4 cells in 100 $\mu$l of medium were then added to each well. The CPE was examined after incubation at 37° C. for 5 days. All virus titers were calculated by the method of Reed and Muench (L. J. Reed et al. Am. J. Hyg. 27, 493–497, 1938) and expressed as 50% cell culture infective dose per ml ($CCID_{50}$ per ml). Chlamydia trachomatis was titrated by inoculation of 10-fold dilutions into monolayers of McCoy cells in 24-well Corning multidishes (Corning, N.Y., U.S.A.). After inoculation the dishes were centrifuged at 1100×G for 75 minutes at 35° C. and then incubated at 37° C. for 2 hrs in a $CO_2$-incubator. The cultures were then changed to fresh culture medium containing 2 $\mu$g/ml of cycloheximide and incubated for 3 days at 37° C. in a $CO_2$-incubator. The monolayers were stained with Lugol's iodine or fluorescein-conjugated monoclonal antibodies against C. trachomatis and the number of inclusions counted. The titer is expressed as inclusion forming units (IFU) per ml.

Assay of Virucidal/microbicidal Activity in Culture Medium

In assays of HSV-1 and VV, 200 $\mu$l of a test compound, either a suspension of fatty acids or monoglycerides in MM or a gel preparation, were placed in a 35 mm tissue culture dish (Nunc) and 200 $\mu$l of virus suspension in MM was added. The virus was mixed with the compound at room temperature by pipetting and stirring. At various time intervals 100 $\mu$l samples were withdrawn, immediately diluted 10-fold in MM and titrated. The lowest inoculated dilution was $10^{-2}$ due to the cytotoxic effect of the lipids. Virus mixed with MM alone was used as a control. The difference between the titer ($log_{10}$) of the control and titers of virus mixed with test compounds, i.e. the reduction of virus titer, was used as a measure of virucidal activity of a compound. Assays of C. trachomatis were done in the same way. In assays of HIV-1, 100 $\mu$l of virus suspension were pipetted into 12×75 mm polystyrene round-bottom tubes (Falcon), and 100 $\mu$l of a gel preparation added. The virus and gel were thoroughly mixed together by pipetting and stirring for 1 minute. Then, 0.8 ml of medium were added to the tube and the diluted mixture pipetted into a tissue culture plate for titration. Virucidal activity was expressed in the same way as for HSV-1, VV and C. trachomatis.

Assay of Virucidal Activity of Gel Preparations in Human Semen

Virus was concentrated 10-fold or more by centrifugation in a Sorvall ultracentrifuge at 100,000 G for 90 minutes. The pellet was resuspended in MM, clarified at 3000 rpm for 10 min, and the concentrated virus stored in aliquots at −80° C. In order to test the virucidal activity of gel preparations against free virus in semen, concentrated virus was diluted 10-fold in fresh (<2 hrs) human semen and 200 $\mu$l of the virus-spiked semen mixed with an equal volume of a gel preparation in a tissue culture dish (HSV-1) or a test tube (HIV-1), as previously described. Samples were withdrawn at intervals and titrated. Virus-spiked semen mixed with m.m. was used as a control.

Evaluation of Toxic Effects of Gel Preparations in Monolayers of CV-1 Cells

Tenfold dilutions of gel formulations were added to monolayers of CV-1 cells, 4 wells per dilution, and the cell layers examined for lysis or other toxic effects after 1 hr, 24 hrs and 48 hrs.

Assay of Cytocidal Activity of Gel Preparations in Human Semen

Human white blood cells (HBC) were separated from heparinized blood by sedimentation on Histopaque-1077 (Sigma). The washed pellet was suspended in human semen at a density of $40 \times 10^6$ cells per millilitre. 200 $\mu$l of this highly leukocytospermic preparation were added to 200 $\mu$l of a gel preparation in a tissue culture dish at room temperiture and mixed with the gel for 1 min. A 100 $\mu$l sample was then immediately diluted 10-fold in MM, stained with an equal volume of 0.5% trypan blue and the number of viable cells counted.

Testing of Vaginal Irritation

Toxic effects of virucidal gels were tested in the vaginas of mice and rabbits. Young female mice (white) weighing 16–18 grams were used. Their vaginas were completely filled with about 100 $\mu$l of each gel preparations which were injected with a 1 ml tuberculine syringe with a blunt metal tip (Endo-Eze Tips, 18 gauge, Ultradent Products, Inc, USA). Two mice were injected with each preparation daily for 8 days. Two control mice received 100 $\mu$l of phosphate buffered saline (PBS) in the same way. The mice were sacrificed at the end of the treatment and their genital tracts dissected out and examined. They were then fixed in 4% formaldehyde in PBS, embedded in paraffin and sections stained with hematoxylin and eosin for microscopic examination.

Young female rabbits (3–4 months) were tested in the same manner except that about 300–400 $\mu$l of a gel preparation were injected into their vaginas with a 1 ml tuberculine syringe without a tip. The treatment was continued daily for 10 days. The animals were then sacrificed and their vaginal mucosas examined both macro- and microscopically.

Results

TABLE 1. Formulations used in the examples (values expressed as percentages are by weight calculated on the formulation)

| | | | |
|---|---|---|---|
| 1A | Glycofurol 75 | 30% | |
| | Monocaprin | 0 mM (control)/10 mM/20 mM | |
| | NaCMC | 2% | |
| | Povidone K30 | 1.0% | |
| | H₂O | ad 25 g | |
| 1B | Glycofurol 75 | 30% | |
| | Monocaprin | 0 mM (control)/10 mM/20 mM | |
| | NaCMC | 2% | |
| | Povidone K30 | 1.0% | |
| | Lactic acid | 0.12% | |
| | H₂O | ad 25 g | |
| 1C | Glycofurol 75 | 27.5% | |
| | Monocaprin | 0 mM (control)/10 mM | |
| | NaCMC | 1.75% | |
| | Povidone K30 | 1.0% | |
| | Lactic acid | 0.098% | |
| | H₂O | ad 25 g | |
| 1D | Glycofurol 75 | 20% | |
| | PEG 200 | 15% | |
| | Monocaprin | 0 mM (control)/10 mM | |
| | NaCMC | 1.75% | |
| | Povidone K30 | 1.0% | |
| | Lactic acid | 0.098% | |
| | H₂O | ad 25 g | |
| 1E | Povidone K30 | 0.5 g | 1.0% |
| | Propylene glycol | 35.0 g | 70% |
| | NaCMC high visc. | 0.5 g | 1.0% |
| | Monocaprin | 0 mM (control/10 mM/20 mM | |
| | H₂O | ad 50 g (13–14 g) | 28% |
| 1F | Povidone K30 | 0.25 g | 1.0% |
| | Propylene glycol | 17.5 g | 70% |
| | NaCMC high visc. | 0.3125 g | 1.25% |
| | Monocaprin | 0 mM (control/20 mM | |
| | H₂O | ad 25 g | |
| 1G | Povidone K30 | 0.25 g | 1.0% |
| | Propylene glycol | 17.5 g | 70% |
| | NaCMC high visc. | 0.375 g | 1.5% |
| | Monocaprin | 0 mM (control)/20 mM | |
| | H₂O | ad 25 g | |
| 1H | Propylene glycol | 5% | |
| | Monocaprin | 0 mM (control/20 mM | |
| | Povidone K30 | 1.0% | |
| | NaCMC high visc. | 2% | |
| | Tween 80 | 2% | |
| | H₂O | ad 30 g | |
| 1I | Propylene glycol | 5% | |
| | Monocaprin | 0 mM (control/20 mM | |
| | Povidone K30 | 1.0% | |
| | NaCMC high visc. | 2% | |
| | Cremophor RH 40 | 5% | |
| | H₂O | ad 30 g | |
| 1J | Glycofurol 75 | 10% | |
| | Monocaprin | 0 mM (control)/10 mM | |
| | NaCMC | 2% | |
| | Povidone K30 | 1.0% | |
| | Cremophor EL | 1% | |
| | H₂O | ad 25 g | |
| 1K | Glycofurol 75 | 30% | |
| | Monocaprin | 0 mM (control/10 mM | |
| | NaCMC | 2% | |
| | Povidone K30 | 1.0% | |
| | Cremophor EL | 1% | |
| | H₂O | ad 25 g | |
| 1L | Ethanol | 10% | |
| | Monocaprin | 0 mM (control/10 mM | |
| | NaCMC | 2% | |
| | Povidone K30 | 1.0% | |
| | Cremophor EL | 1% | |
| | H₂O | ad 25 g | |
| 1M | Monocaprin | 0 mM (control)/10 mM | |
| | NaCMC | 2% | |
| | Povidone K30 | 1.0% | |

|     |                              | -continued |                            |        |
| --- | ---------------------------- | ---------- | -------------------------- | ------ |
|     | 2-HPβC                       | 3.5%       |                            |        |
|     | H₂O                          | ad 25 g    |                            |        |
| 1N  | Glycofurol 75                | 5%         |                            |        |
|     | Ethanol                      | 5%         |                            |        |
|     | Monocaprin                   | 0          | mM (control)/10 mM         |        |
|     | NaCMC                        | 2%         |                            |        |
|     | Povidone K30                 | 1.0%       |                            |        |
|     | Cremophor EL                 | 1%         |                            |        |
|     | H₂O                          | ad 25 g    |                            |        |
| 1P  | Glycofurol 75                | 30%        |                            |        |
|     | Monocaprin                   | 20         | mM                         |        |
|     | Propyl parahydroxybenzoic acid | 0.02%    |                            |        |
|     | Methyl parahydroxybenzoic acid | 0.08%    |                            |        |
|     | NaCMC                        | 1.75%      |                            |        |
|     | Povidone K30                 | 1%         |                            |        |
|     | H₂O                          | ad 100%    |                            |        |
| 1Q  | Glycofurol 75                | 30%        |                            |        |
|     | Monocaprin                   | 20         | mM                         |        |
|     | Propyl parahydroxybenzoic acid | 0.02%    |                            |        |
|     | Methyl parahydroxybenzoic acid | 0.08%    |                            |        |
|     | NaCMC                        | 1.75%      |                            |        |
|     | Povidone K30                 | 1%         |                            |        |
|     | 9%/w/v) lactic acid solution | 1.2%       |                            |        |
|     | H₂O                          | ad 100%    |                            |        |
| 1R  | Glycofurol 75                | 80%        |                            |        |
|     | Monocaprin                   | 20         | mM                         |        |
|     | Propyl parahydroxybenzoic acid | 0.02%    |                            |        |
|     | Methyl parahydroxybenzoic acid | 0.08%    |                            |        |
|     | NaCMC                        | 3.4%       |                            |        |
|     | Povidone K30                 | 1.7%       |                            |        |
|     | 9% (w/v) lactic acid solution | 1.2%      |                            |        |
|     | 0.3M citrate buffer solution | 10%        |                            |        |
|     | H₂O                          | ad 100%    |                            |        |
| 1S  | Glycofurol 75                | 30%        |                            |        |
|     | Monocaprin                   | 20         | mM                         |        |
|     | Propyl parahydroxybenzoic acid | 0.02%    |                            |        |
|     | Methyl parahydroxybenzoic acid | 0.08%    |                            |        |
|     | NaCMC                        | 3.4%       |                            |        |
|     | Povidone K30                 | 1.7%       |                            |        |
|     | Tween 20                     | 1%         |                            |        |
|     | 9% (w/v) lactic acid solution | 1.2%      |                            |        |
|     | 0.3M citrate buffer solution | 10%        |                            |        |
|     | H₂O                          | ad 100%    |                            |        |
| 1T  | Glycofurol 75                | 30%        |                            |        |
|     | Monocaprin                   | 0          | mM (control)/20 mM         |        |
|     | NaCMC                        | 3.4%       |                            |        |
|     | Povidone K30                 | 1.7%       |                            |        |
|     | 9% (w/v) lactic acid         | 4%         |                            |        |
|     | Citrate buffer               | 1.2M       |                            |        |
|     | Tween 20                     | 1%         |                            |        |
|     | H₂O                          | ad 100%    |                            |        |
| 2A  | Glycofurol 75                | 30%        |                            |        |
|     | Monocaprin                   | 0          | mM (control/10 mM/20 mM    |        |
|     | HPMC                         | 1%         |                            |        |
|     | Carbopol 934                 | 0.5%       |                            |        |
|     | 2% NaOH                      | ad pH 5.1–5.3 |                         |        |
|     | H₂O                          | ad 25 g    |                            |        |
| 2B  | HPMC                         | 0.4 g      |                            | 0.8%   |
|     | Carbopol 934                 | 0.12 g     |                            | 0.24%  |
|     | Propylene glycol             | 30.0 g     |                            | 60.0%  |
|     | H₂O                          | 10 + 10 g  |                            | 40.0%  |
|     | Monocaprin                   | 0          | mM (control)/10 mM/20 mM   |        |
|     | 2% NaOH                      | ad pH 7    |                            |        |
|     | Propylene glycol             | ad 50 g    |                            |        |
| 2C  | HPMC                         | 0.25 g     |                            | 1.0%   |
|     | Carbopol 934                 | 0.06 g     |                            | 0.24%  |
|     | Propylene glycol             | 15 g       |                            | 60%    |
|     | H₂O                          | 10 g       |                            | 40%    |
|     | Monocaprin                   | 0          | mM (control/20 mM          |        |
|     | 2% NaOH                      | ad pH 7    |                            |        |
|     | Propylene glycol             | ad 25 g    |                            |        |
| 2D  | HPMC                         | 1%         |                            |        |
|     | Carbopol 934                 | 0.24%      |                            |        |
|     | Monocaprin                   | 0          | mM (control)/10 mM         |        |
|     | 2-HPβC                       | 3.5%       |                            |        |
|     | 2% NaOH                      | ad pH 7    |                            |        |
|     | H₂O                          | ad 25 g    |                            |        |
| 2E  | HPMC                         | 1%         |                            |        |
|     | Carbopol 934                 | 0.5%       |                            |        |

-continued

| | |
|---|---|
| Monocaprin | 20 mM |
| Glycofurol 75 | 80% |
| Propyl parahydroxybenzoic acid | 0.02% |
| Methyl parahydroxybenzoic acid | 0.08% |
| 0.5M NaOH | ad pH 4.9–5.1 |
| 0.3M citrate buffer solution | 10% |
| $H_2O$ | ad 100% |

EXAMPLE 1

Virucidal Activities of Fatty Acids and Monoglycerides and Combinations Thereof The lipids were dissolved in ethanol at a concentration of 1 M and stored at 4° C. In each experiment they were suspended in MM by vortexing at the highest speed for 1 min. Suspensions of different lipids and mixtures of lipids in varying concentrations were tested for virucidal activity in MM against HSV-1 and VV as described in the Materials and Methods section. The results are given in Table 2 below.

TABLE 2

Inactivation of HSV-1 and VV by incubation at room temperature for 1 minute with lipids and lipid mixtures containing various combinations of fatty acids and monoglycerides in MM.

| | Conc. | Reduction of virus titer,$\log_{10}$ | |
|---|---|---|---|
| Lipid/lipid mixture | (mM) | HSV-1 | VV |
| 1. Monocaprin | 20 | >5.8 | 3.8 |
| 2. Monocaprin | 10 | >5.3 | 2.4 |
| 3. Monocaprin | 5 | >5.5 | not done |
| 4. Monocaprin | 2.5 | 2.2 | not done |
| 5. Capric acid | 20 | <0.5 | not done |
| 6. Caprylic acid 1-monoglyceride | 20 | 0.5 | not done |
| 7. Capriylic acid 1-monoglyceride | 10 | 0 | not done |
| 8. Lauric acid 1-monoglyceride | 20 | 3.1 | not done |
| 9. Lauric acid 1-monoglyceride | 10 | 3.5 | not done |
| 10. Lauric acid 1-monoglyceride | 5 | 3.0 | not done |
| 11. Lauric acid | 20 | >5.8 | not done |
| 12. Lauric acid | 10 | <1.5 | not done |
| 13. Monocaprin<br>Lauric acid 1-monoglyceride | 5<br>5 | 4.8 | not done |
| 14. Oleic acid 1-monoglyceride | 20 | <1.0 | not done |
| 15. Oleic acid 1-monoglyceride | 10 | <1.0 | not done |
| 16. Oleic acid | 20 | <1.0 | not done |
| 17. Oleic acid | 10 | <1.0 | not done |
| 18. Palmitoleic acid 1-monoglyceride<br>Oleic acid 1-monoglyceride | 10<br>10 | <1.0 | 0.7 |
| 19. Palmitoleic acid<br>Oleic acid | 10<br>10 | >5.0 | 1.4 |
| 20. Palmitoleic acid<br>Oleic acid | 5<br>5 | <1.0 | 0.2 |
| 21. Palmitoleic acid 1-monoglyceride<br>Oleic acid 1-monoglyceride<br>Palmitoleic acid<br>Oleic acid | 5<br>5<br>5<br>5 | 1.5 | 1.2 |
| 22. Palmitoleic acid | 5 | <1.0 | not done |
| 23. Palmitoleic acid | 10 | >5.0 | not done |

TABLE 2-continued

Inactivation of HSV-1 and VV by incubation at room temperature for 1 minute with lipids and lipid mixtures containing various combinations of fatty acids and monoglycerides in MM.

| | Conc. | Reduction of virus titer,$\log_{10}$ | |
|---|---|---|---|
| Lipid/lipid mixture | (mM) | HSV-1 | VV |
| 24. Palmitoleic acid 1-monoglyceride | 10 | 0 | 0.7 |
| 25. Palmitoleic acid 1-monoglyceride | 20 | 0 | not done |
| 26. Myristic acid | 10 | 0 | not done |
| 27. Myristic acid | 20 | 0 | not done |

It can be seen from Table 2 that monocaprin was the most active monoglyceride and was still fully active against HSV-1 at a concentration of 5 mM for 1 minute. Lauric acid and palmitoleic acid also caused a greater than $10^5$-fold inactivation of HSV-1 but lost their activities at concentrations of 10 mM and 5 mM, respectively. Also a mixture of palmtoleic acid and oleic acid at a concentration of 20 mM was active, particularly against HSV-1. However, the activity was lost when the total concentration of these unsaturated fatty acids was lowered to 10 mM. The lipids which were tested against VV showed less activity against VV than against HSV-1.

EXAMPLE 2

Inactivation of HSV-1 Mixed 1:9 With Human Semen

Monocaprin, lauric acid 1-monoglyceride and caprylic acid 1-monoglyceride were tested against HSV-1 diluted in semen. As shown in Table 3, monocaprin at a concentration of 10 mM is more active than 20 mM of caprylic acid 1-monoglyceride and lauric acid 1-monoglyceride. It is also noted that monocaprin is less active against HSV-1 in semen than in MM (see Table 2)

TABLE 3

Inactivation of HSV-1 in human semen by incubation with monoglycerides at room temperature for 1 minute.

| Monoglyceride | Conc. (mM) | Reduction of HSV-1 titer, $\log_{10}$ |
|---|---|---|
| Monocaprin | 20 | >4.0 |
| Monocaprin | 10 | 3.0 |
| Caprylic acid 1-monoglyceride | 20 | 1.0 |
| Lauric acid 1-monoglyceride | 20 | 2.0 |

EXAMPLE 3

Virucidal Activities of Gel Preparations Containing 1-monocaprin

Since monocaprin (MC) was most active against HSV-1 as shown in Tables 2 and 3, this monoglyceride was selected as the active ingredient in pharmaceutical gel formulations designed as carrier vehicles. Gel formulations 1A, 1B, and 2A containing MC in various concentrations were tested against HSV-1 in MM after incubation for varying lengths of time. The results are shown in Table 4.

TABLE 4

Inactivation of HSV-1 in MM by incubation at room temperature with gel formulations 1A, 1B, and 2A without active ingredient or containing various concentrations of MC.

| Formulation | Conc. of MC (mM) | Contact time (min) | Reduction of virus titer, $\log_{10}$ |
|---|---|---|---|
| 1A | 0 | 1 | 0.4 |
|  | 0 | 5 | 0.5 |
|  | 0 | 10 | 0.6 |
|  | 2.5 | 1 | <0.8 |
|  | 2.5 | 5 | 2.0 |
|  | 2.5 | 10 | 2.3 |
|  | 5 | 1 | >5.2 |
|  | 5 | 5 | >5.2 |
|  | 10 | 1 | >5.2 |
|  | 20 | 1 | >5.2 |
| 1B | 0 | 1 | 0.2 |
|  | 0 | 5 | 0.4 |
|  | 0 | 10 | 0.3 |
|  | 2.5 | 1 | 1.0 |
|  | 2.5 | 5 | 1.0 |
|  | 2.5 | 10 | 2.0 |
|  | 5 | 1 | >5.2 |
|  | 5 | 5 | >5.2 |
|  | 10 | 1 | >5.2 |
|  | 20 | 1 | >5.2 |
| 2A | 0 | 1 | 0.2 |
|  | 0 | 5 | 1.0 |
|  | 0 | 10 | 2.3 |
|  | 2.5 | 1 | 3.3 |
|  | 2.5 | 5 | >4.8 |
|  | 2.5 | 10 | >4.8 |
|  | 5 | 1 | >5.2 |
|  | 5 | 5 | >5.2 |
|  | 10 | 1 | >5.2 |
|  | 20 | 1 | >5.2 |

Gel formulations without MC had no or only a very slight activity against HSV-1 in MM, whereas gels with an MC concentration of 5 mM or more were highly active even after contact with the virus for only 1 minute.

EXAMPLE 4

Virucidal Activities of Gel Formulations Against HSV-1 Mixed 1:9 With Human Semen The activities of the same gel formulations against HSV-1 in human semen were similarly tested and the results are shown in Table 5.

TABLE 5

Inactivation of HSV-1 in human semen by incubation at room temperature with gel formulations 1A, 1B, and 2A without active ingredient or containing various concentrations of MC.

| Formulation | Conc. of MC (mM) | Contact time (min) | Reduction of virus titer, $\log_{10}$[1] |
|---|---|---|---|
| 1A | 0 | 10 | 0 |
|  | 5 | 1 | 1.5 |
|  | 5 | 5 | 2.4 |
|  | 5 | 10 | 2.3 |
|  | 10 | 1 | 2.9 |
|  | 10 | 5 | 4.2 |
|  | 10 | 10 | >5.0 |
|  | 20 | 1 | >5.5 |
|  | 20 | 5 | >5.5 |
|  | 20 | 10 | >5.5 |
| 1B | 0 | 10 | 0 |
|  | 5 | 1 | 1.0 |
|  | 5 | 5 | 1.1 |
|  | 5 | 10 | 1.0 |
|  | 10 | 1 | 2.8 |
|  | 10 | 5 | 4.4 |
|  | 10 | 10 | >5.0 |
|  | 20 | 1 | >4.8 |
|  | 20 | 5 | >5.5 |
|  | 20 | 10 | >5.5 |
| 2A | 0 | 10 | 0 |
|  | 5 | 1 | 1.1 |
|  | 5 | 5 | 1.2 |
|  | 5 | 10 | 1.6 |
|  | 10 | 1 | 3.2 |
|  | 10 | 5 | >5.0 |
|  | 10 | 10 | >5.5 |
|  | 20 | 1 | >5.0 |
|  | 20 | 5 | >5.5 |
|  | 20 | 10 | >5.5 |

[1]Mean of 3 experiments

By comparing Tables 4 and 5 it can be seen that the MC-containing gels are less active against HSV-1 in semen than in MM. It is also seen that 20 mM of MC is the optimal concentration for inactivation of virus after contact for 1 min.

EXAMPLE 5

A Comparison of Virucidal Activities of Gel Formulations of Different Compositions A number of different gel formulations were tested against HSV-1 suspended in MM and mixed with the gels for 1 minute at room temperature. The results are shown in Table 6.

TABLE 6

Inactivation of HSV-1 in MM by incubation at room temperature for 1 minute with various gel formations with or without MC.

| Formulation | Conc. of MC (mM) | Reduction of virus titer, $\log_{10}$ |
|---|---|---|
| 1A | 0 | 0.6 |
|  | 10 | >5.2 |
| 1B | 0 | 0.2 |
|  | 10 | >5.2 |
| 1C | 0 | 0 |
|  | 10 | 1.7 |
| 1D | 0 | 0.2 |
|  | 10 | 0.5 |
| 1E | 0 | 0.5 |
|  | 10 | 2.2 |
|  | 20 | >4.2 |
| 1F | 0 | 0.5 |
|  | 20 | >5.0 |
| 1G | 0 | 0.2 |
|  | 20 | >4.5 |
| 1H | 0 | 0.2 |
|  | 20 | <1.0 |

TABLE 6-continued

Inactivation of HSV-1 in MM by incubation at room temperature for 1 minute with various gel formations with or without MC.

| Formulation | Conc. of MC (mM) | Reduction of virus titer,$\log_{10}$ |
|---|---|---|
| 1I | 0 | 0.1 |
|  | 20 | <0.8 |
| 1J | 0 | 0.6 |
|  | 10 | <0.8 |
| 1K | 0 | 0.3 |
|  | 10 | <0.8 |
| 1L | 0 | 0.3 |
|  | 10 | <0.8 |
| 1M | 0 | 0 |
|  | 10 | <0.8 |
| 1N | 0 | 0 |
|  | 10 | <0.8 |
| 1P | 0 | 0.7 |
|  | 10 | <5.5 |
| 1R | 0 | 0.3 |
|  | 10 | >5.5 |
| 1T | 0 | 0 |
|  | 10 | >5.8 |
| 2A | 0 | 0.2 |
|  | 10 | >5.2 |
| 2B | 0 | 0.2 |
|  | 10 | 2.2 |
|  | 20 | >4.0 |
| 2C | 0 | 0 |
|  | 20 | >4.5 |
| 2D | 0 | 0 |
|  | 10 | <0.8 |
| 2E | 0 | 0.2 |
|  | 20 | >4.5 |

As appears from Table 6, propylene glycol and glycofurol 75 are suitable as solvents for MC in gels with either povidone or carbopol 934 as a gelling agent. Addition of surfactants like cremophor or complex forming agents like 2-HBβC inhibits the activity of MC in the gels. However, addition of Tween 20 (formulation 1T) and preservatives (formulations 1P and 1R) did not decrease the activity of MC in the formulations.

EXAMPLE 6

Virucidal Activity of Gel Formulations Against HIV-1 in Culture Medium and Human Semen Gel formulations which had been found to inactivate HSV-1 in MM (Table 6) were tested against HIV-1 in culture medium as described in the Materials and Methods section. The results are shown in Table 7.

TABLE 7

Inactivation of HIV-1 in culture medium by incubation for 1 minute at room temperature with gel formulations with or without MC.

| Formulation | Conc. of MC (mM) | Reduction of virus titer,$\log_{10}$ |
|---|---|---|
| 1F | 0 | 0.5 |
|  | 20 | >4.0 |
| 2C | 0 | 1.2 |
|  | 20 | >4.0 |

Both gels with 20 mM MC inactivated HIV-1 more than 10,000-fold. The carbopol-based gel without MC (1F) had a slight virucidal activity, whereas the povidon-based gel (2C) was without a significant effect. Both gels contained propylene glycol as a solvent. Similar results, i.e. about 10,000-fold reduction in titer, were obtained with gel formulations 1P and 2E (containing 20 mM MC dissolved in glycofurol 75) mixed for 1 or 2 minutes with HIV-1 diluted 1:10 either in medium or in human semen. The results are shown in Table 7A.

TABLE 7A

Inactivation of HIV-1 diluted 10-fold in culture medium or in human semen and incubated with gel formulations for 1 or 2 minutes at room temperature.

| Formu-lation | Conc. of MC (mM) | Contact time (min) | Red. of virus titer,$\log_{10}$ in medium | semen 1 | 2 | 3 |
|---|---|---|---|---|---|---|
| 1P | 0 | 1 | 0.6 | * | 0.8 | * |
|  | 0 | 2 | * | 0.7 | * | 1.2 |
|  | 20 | 1 | >4.8 | * | >4.0 | >4.2 |
|  | 20 | 2 | * | >2.8 | * | >4.3 |
| 1R | 0 | 1 | * | * | * | * |
|  | 0 | 2 | * | * | * | 0.3 |
|  | 20 | 1 | * | * | * | >3.6 |
|  | 20 | 2 | * | * | * | >3.9 |
| 2E | 0 | 1 | 0.6 | * | 0.5 | * |
|  | 0 | 2 | * | 0 | * | 1.3 |
|  | 20 | 1 | >4.8 | * | <3.5 | >4.1 |
|  | 20 | 2 | * | 3.9 | * | >3.6 |

*: Not done

Table 7A shows that the gel formulations inactivated HIV-1 in human semen, but not as efficiently as in the medium. This is in agreement with data on the inactivation of HSV-1 in MM and semen (Tables 4 and 5). There was no difference in HIV-1 inactivation after incubation with the gel formulations for 1 and 2 minutes, respectively.

EXAMPLE 7

Toxic Effect of Gel Preparations in Cell Monolayers

Tenfold dilutions of gel formulations were added to CV-1 monolayers and the cytotoxicity evaluated by microscopic examination of live cells. The results are shown in Table 8.

TABLE 8

Cytotoxic effects of gel formulations, with or without MC in CV-1 cell monolayers.

| Formulation | Conc. of MC (mM) | Cytotoxic dilution 1 h | 24 h | 48 h |
|---|---|---|---|---|
| 1A | 0 | $(10^{-1})$* | $10^{-1}$ | $10^{-1}$ |
|  | 10 | $10^{-1}$** | $10^{-1}$ | $10^{-1}$ |
|  | 20 | $10^{-1}$ | $10^{-1}$ | $10^{-1}$ |
| 2A | 0 | $(10^{-1})$ | $10^{-1}$ | $10^{-1}$ |
|  | 20 | $10^{-1}$ | $10^{-1}$ | $10^{-1}$ |
| Gynol-plus*** |  | $10^{-2}$ | $10^{-3}$ | $10^{-3}$ |

*In parenthesis: round cells, not layed
**Without parenthesis: complete lysis of cells
***A commercial (Cilag AG, Schaffhausen, Switzerland) spermicidal gel containing 2% nonoxynol-9 in povidone K 30 and propylene glycol.

*In parenthesis: round cells, not lysed
** Without parenthesis: complete lysis of cells
***A commercial (Cilag AG, Schaffhausen, Switzerland) spermicidal gel containing 2% nonoxynol-9 in povidone K 30 and propylene glycol.

From Table 8 it can be seen that 10-fold dilutions of all the gels lysed the cell monolayers after incubation for 24 hrs. No visible toxic effect was seen in higher dilutions even after incubation for 4 days. Gels without MC were less toxic after incubation for 1 hr but had lysed the cell layers after 24 hrs. A vaginal gel (Gynol-plus), which contains 2% nonoxynol-9, caused a complete lysis of the cell layers in 1 hr at dilution $10^{-2}$ and in 24 hrs at dilution $10^{-3}$. It was therefore 10–100-fold more cytotoxic to the cell monolayers than the virucidal gel formulations containing 20 mM (0.5%) MC.

EXAMPLE 8

Killing of Leukocytes in Human Semen

It is important that a virucidal gel kills not only free virus but also lymphocytes or monocytes in semen which may be infected with HIV. Gel formulations which are active against free virus in semen were therefore tested for cytocidal activity in semen. The white blood cell (WBC) counts in most normal ejaculates are below $10^6$ cells per ml (H. Wolff, The biological significance of white blood cells in semen, Fert. Ster. 63, 1143–1157, 195). Since this number is too low to demonstrate a significant cytocidal effect of the gels, WBC were isolated from human blood by sedimentation on Histopaque-1077 (Sigma) and added to the semen in a number of $40 \times 10^6$ WBC per ml. Table 9 shows the activity of virucidal gels in killing these cells.

TABLE 9

Killing of human WBC in semen by incubation at room temperature for 1 minute with various gel formulations, with or without MC.

| Formulation | Conc. of MC (mM) | WBC/ml | Reduction of WBC count |
|---|---|---|---|
| 1A | 0 | $42 \times 10^6$ | none |
|    | 10 | $<40 \times 10^2$ | $>10^4$-fold |
| 2A | 0 | $56 \times 10^6$ | none |
|    | 20 | $<40 \times 10^2$ | $>10^4$-fold |

The semen samples used in repeated experiments had cell counts of $2–5 \times 10^5$ cells per ml before addition of WBC. After treatment with the active gels for 1 min a large number of fields were examined under the microscope without detection of a single live cell. In contrast, dead cells were observed in large numbers.

EXAMPLE 9

In Vitro Spermicidal Activity of Gel Formulations

Preliminary experiments were done to evaluate the spermicidal activity of various gel formulations. Typical results are shown in Table 10.

TABLE 10

Effect of gel formulations, with and without MC, on sperm motility and viability in semen mixed with gels in the ratio 1:2 (volume gel:volume semen) and incubated at room temperature.

| Formulation | Conc. of MC (mM) | % motility* 2 | 5 | 10 min | % viability** 10 min |
|---|---|---|---|---|---|
| 1E | 0 | 25 | 25 | not done | 49 |
|    | 10 | 0 | 0 | not done | 6 |
|    | 20 | 0 | 0 | not done | 0 |
| 2B | 0 | 30 | 30 | 30 | 52 |
|    | 10 | 20 | 20 | 15 | 16 |
|    | 20 | 10 | <5 | 0 | 2 |

*Sperm cell count in the semen was $2 \times 10^8$ per ml with 40% motility
**Vital staining (eosin)

Similar results were obtained with other semen samples tested against gel formulations 1F, 1G, and 2C. The results are shown in Table 10A. In most experiments the sperm cell motility decreased to zero in less than 10 min in gel formulations containing 20 mM monocaprin. The viability decreased to less than 2% in 10 minutes in the same gel formulations.

TABLE 10A

Effect of gel formulations, with and without MC, on sperm motility and viability in semen mixed with gels in the ratio 1:3 (volume gel:volume semen) and incubated at room temperature for 10 minutes.

| Formulation | Conc. of MC (mM) | % motility* | % viability** |
|---|---|---|---|
| 1F | 0 | 10 | 41 |
|    | 20 | 0 | 2 |
| 1G | 0 | 15 | 35 |
|    | 20 | 0 | 0 |
| 2C | 0 | 10 | 36 |
|    | 20 | 0 | 4 |

*Sperm cell count in the semen was $3 \times 10^7$ per ml with 30% motility
**Vital staining (eosin)

EXAMPLE 10

Inactivation of C. Trachomatis by Monoglycerides

Caprylic acid 1-monoglyceride, monocaprin and lauric acid 1-monoglyceride were tested against C. tracomatis by incubation at 37° C. for 10 minutes as described in the Materials and Methods section. The results are shown in Table 11.

TABLE 11

Inactivation of C. trachomatis by various concentrations of monoglycerides in medium at 37° C. for 10 minutes.

| Monoglyceride | Concentration (mM) | Reduction of IFU* ($\log_{10}$) |
|---|---|---|
| Caprylic acid 1-monoglyceride | 5 | 0.1 |
|  | 10 | 0.3 |
|  | 20 | 0.2 |
| Monocaprin | 5 | >5.6 |
|  | 10 | >5.6 |
|  | 20 | >4.6 |
| Lauric acid 1-monoglyceride | 5 | 0.5 |
|  | 10 | 0.7 |
|  | 20 | 0.5 |

*IFU: Inclusion Forming Units

It can be seen from Table 11 that only monocaprin was able to inactivate the bacteria. This is in agreement with the effect of these monoglycerides on HSV-1 (Table 2), except that lauric acid 1-monoglyceride is more active against HSV-1 than against C. trachomatis.

EXAMPLE 11

Inactivation of C. Trachomatis in Gel Formulations Containing MC.

Based on the results obtained in Example 10, gel formulations containing various concentrations of monocaprin were tested against *C. trachomatis*. The results are shown in Table 12.

TABLE 12

Inactivation of *C. trachomatis* by incubation for 10 minutes at 37° C. with gel formulations 1A and 2A.

| Formulation | Conc. of MC | Reduction of IFU ($\log_{10}$) |
|---|---|---|
| 1A | 0 | 0.8 |
|  | 5 | 5.2 |
|  | 10 | >5.7 |
|  | 20 | >4.7 |
| 2A | 0 | 2.4 |
|  | 5 | 2.1 |
|  | 10 | >5.6 |
|  | 20 | >4.6 |

Both formulations were very active against the bacteria at MC concentrations of 10 and 20 mM which are also the most active concentrations against HSV-1 (Table 4). However, 5 mM MC was less active in formulation 2A than in the medium (Table 11) and the formulation 2A without MC significantly reduced the infectivity of the bacteria during incubation at 37° C. for 10 minutes.

EXAMPLE 12

Toxicity of Gel Preparations in Vaginal Mucosas of Mice and Rabbits

Gel formulations which showed virucidal activities against HSV-1 in semen were tested for toxic effects in vaginal mucosas as described in the Materials and Methods section. The results are shown in Table 13.

TABLE 13

Toxic effects of gel formulations, with or without MC, on vaginal mucosas of mice or rabbits, as observed macroscopically or by microscopic examination of stained preparations from the vaginal epithelium.

| Formulation | Conc. of MC (mM) | Macroscopic lesions (r/m)* | Microscopic lesions (r/m)* |
|---|---|---|---|
| 1F | 0 | + (r) | — |
|  | 20 | 2+ (r) | — |
| 2C | 0 | + (r) | — |
|  | 20 | 2+ (r) | — |
| 1A | 0 | none (m) | (+) |
|  | 10 | none (m) | (+) |
|  | 20 | none (m) | (+) |

*r: tested in rabbits.
m: tested in mice.

In Table 13, + indicates a widespread redness of the mucosa which was in sharp contrast to a slight redness observed in the vaginal mucosa of control rabbits which received a saline solution (0.9% NaCl in water). 2+ indicates a higher degree of redness with apparent ulceration. Gel formulations 1F and 2C, which contain propylene glycol as a solvent for MC, are therefore toxic for the rabbit mucosa, and the toxicity is increased in gels containing 20 mM of MC.

Mouse vaginal mucosas treated with gel formulation 1A, with or without MC, looked normal by macroscopic examination and apparently identical to mucosas of control mice treated with a saline solution. Histologically, epithelium from all treated mice looked similar. Mild acute superficial inflammation was observed with a slight infiltration of neutrophilic granulocytes (+). Since mice treated with gel formulations showed the same degree of inflammatory changes as the control mice, they most likely are non-specific and caused by mechanical irritation by the metal tip used for injection. It can therefore be concluded that gel formulation 1A, which is povidone based and contains 30% glycofurol 75 as a solvent, is not toxic to the vaginal mucosas of mice, even when it contains 10 or 20 mM of MC.

DISCUSSION AND CONCLUSION

Pharmaceutical formulations have been designed which are suitable for killing enveloped viruses in culture medium and/or human semen at a high ratio and in a short time, i.e. $>10^4$-fold within 1 minute. Similar results were also obtained with *Chlamydia trachomatis*. The formulations also kill human white blood cells in human semen at a high ratio and in a short time, i.e. $>10^4$-fold in 1 minute. Gel formulations containing 20 mM of monocaprin dissolved in 30% glycofurol 75 do not cause a detectable specific irritation in the vaginal mucosa of mice after daily application for 8 days. In contrast, propylene glycol used as a sole solvent in gel preparations in concentrations of 60–70% had toxic effects in the vaginal mucosa of rabbits.

Among the lipids tested, monocaprin was found to be most effective lipid in inactivating HSV-1 in culture medium in 1 minute. However, lauric acid 1-monglyceride and a mixture of palmitoleic acid and oleic acid also showed interesting virucidal activity under these conditions, and lauric acid and palmitoleic acid showed a considerable virudical activity under these conditions. Based on the superior virucidal effect of monocaprin against HSV-1, this lipid was selected as the presently preferred active ingredient in gel formulations.

The representative gel formulations, either sodium carboxymethylcellulose or carbopol based, comprising monocaprin dissolved in glycofurol 75, are interesting vaginal microbicides for protection against sexually transmitted infections by viruses such as HSV and HIV, against Chlamydia and most likely other bacterial sexually transmitted diseases.

As the results reported herein show that the formulations of the invention are useful and show extremely fast effect under conditions which are relevant models for the highly demanding purpose of preventing sexually transmitted diseases, they also strongly indicate the usefulness of the formulations of the invention for preventing or treating infections of other mucosal membranes or skin adjacent thereto, such as those described hereinbefore.

What is claimed is:

1. A method for treating infection of the genital mucosa of a mammal, by virus, pathogenic bacteria or fungi, comprising topically administering, to the genital mucosa of the mammal, an effective prophylactic amount of a formulation comprising a hydrogel which contains a) at least one microbicidal lipid as an active ingredient, wherein the lipid is selected from the group consisting of $C_{6-18}$ fatty acids or salts thereof, $C_{6-18}$ fatty acid monoglycerides, $C_{6-18}$ fatty acid esters of monohydric alcohols, $C_{6-18}$ fatty alcohols, and $C_{6-18}$ fatty alcohol monoglyceride ethers, the $C_{6-18}$ chain containing at least one double or triple bond when the number of carbon atoms thereof exceeds 15, b) at least one water gelling agent selected from the group consisting of polysaccharides, acrylic polymers, proteins and high molecular weight polyhydroxy compounds, and c) at least one solubitizing agent selected from the group consisting of lower polyhydric alcohols, polyalkylene glycols, and polyhydroxy ethers, which solubilizing agent keeps the lipid dissolved in the hydrogel, the formulation being one which when incubated for 5 minutes with HSV-1 in a titer of 100 million $CCID_{50}$ per ml in Cell Culture Maintenance Medium in a concentration corresponding to 5 millimolar lipid will cause at least a thousand fold reaction of the virus titer, or which, when incubated for 1 minute with HIV-1 in a titer of 10 million $CCID_{50}$ per ml in Cell Culture Maintenance Medium in a concentration corresponding to 20 millimolar lipid will cause at least a hundred fold reduction of the virus titer, or which, when incubated for 10 minutes with *C. trachomatis* in a titer of 10 million IFU per ml in Cell Culture Maintenance Medium in a concentration corresponding to 5 millimolar lipid will cause at least a thousand fold reduction of the bacterial titer.

2. A method according to claim 1, wherein the fatty moieties are saturated.

3. A method according to claim 1, wherein the formulation is one which when incubated for 5 minutes with HSV-1 in a titer of 100 million $CCID_{50}$ per ml in Cell Culture Maintenance Medium in a concentration corresponding to 5 millimolar lipid will cause at least a ten thousand fold reduction of the virus titer, or which, when incubated for 1 minute with HIV-1 in a titer of 10 million $CCID_{50}$ per ml in Cell Culture Maintenance Medium in a concentration corresponding to 20 millimolar lipid will cause at least a thousand fold reduction of the virus titer, or which, when incubated for 10 minutes with *C. trachomatis* in a titer of 10 million IFU per ml in Cell Culture Maintenance Medium in a concentration corresponding to 5 millimolar lipid will cause at least a ten thousand fold reduction of the bacterial titer.

4. A method according to claim 3, wherein the formulation is one which when incubated for 5 minutes with HSV-1 in a titer of 100 million $CCID_{50}$ per ml in Cell Culture Maintenance Medium in a concentration corresponding to 5 millimolar lipid will cause at least a hundred thousand fold reduction of the virus titer, or which, when incubated for 1 minute with HIV-1 in a titer of 10 million $CCID_{50}$ per ml in Cell Culture Maintenance Medium in a concentration corresponding to 20 millimolar lipid will cause at least a ten thousand fold reduction of the virus titer, or which, when incubated for 10 minutes with *C. trachomatis* in a titer of 10 million IFU per ml in Cell Culture Maintenance Medium in a concentration corresponding to 5 millimolar lipid will cause at least a hundred thousand fold reduction of the bacterial titer.

5. A method according to claim 1, wherein the lipid is selected from capric acid 1-monoglyceride, lauric acid and palmitoleic acid.

6. A method according to claim 5, wherein the lipid is capric acid 1-monoglyceride.

7. A method according to claim 1, wherein the solubilizing agent is a compound or compounds selected from the group consisting of compounds of the general formula I:

$$R—(O—(CH_2)_n)_m—OH \qquad (I)$$

wherein n is an integer in the range from 1 to 4, m is an integer in the range from 1 to 15, and R is H or $R_1CH_2$, wherein $R_1$ designates a 5- or 6-membered aliphatic ring wherein from one to three carbon atoms may be replaced by the nitrogen and/or oxygen atoms, said 5- or 6-membered ring optionally carrying from one to three substituents selected from the group consisting of halogen, amino, carboxy, and hydroxy;

and compounds of the general formula II:

$$R—(O—CH_2—CH(CH_3))_k—OH \qquad (II)$$

wherein k is an integer in the range from 1 to 15, and R is H or $R_1CH_2$, wherein $R_1$ is as defined above.

8. A method according to claim 7, wherein n is 2 or 3, and R is H or $R_2CH_2$, wherein $R_2$ designates a 5- or 6-membered aliphatic ring wherein from one to three carbon atoms may be replaced by nitrogen and/or oxygen atoms.

9. A method according to claim 8 wherein n is 2, and R is H or $R_3CH_2$, wherein $R_3$ designates a 5- or 6-membered aliphatic ring wherein one or two carbon atoms may be replaced by oxygen atoms.

10. A method according to claim 9, wherein R is H or

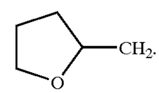

11. A method according to claim 7, wherein m is an integer in the range from 1 to 8.

12. A method according to claim 11, wherein the solubilizing agent is a compound or compounds selected from the group consisting of compounds of the general formula I $$R—(O—CH_2—CH_2)_m—OH \qquad (I)$$

wherein m is an integer in the range from 1 to 4, and R is H or 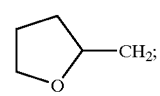 and compounds of the general formula (II)

$$H—(O—CH_2—CH(CH_3))_k—OH \qquad (II)$$

wherein k is an integer in the range from 1 to 4.

13. A method according to claim 12, wherein m is 1 or 2, and k is 1 or 2.

14. A method according to claim 12, wherein the solubilizing agent is selected from the group consisting of tetrahydrofurfuryl alcohol polyethylene glycol ether, ethylene glycol and propylene glycol, and mixtures thereof.

15. A method according to claim 14, wherein the solubilizing agent is tetrahydrofurftryl alcohol polyethylene glycol ether.

16. A method according to claim 1, wherein the lipid is present in the formulation in a concentration of from about 1 to about 40 millimolar.

17. A method according to claim 16, wherein the lipid is present in the formulation in a concentration of about 5–30 millimolar.

18. A method according to claim 17, wherein the lipid is present in the formulation in a concentration of about 10–25 millimolar.

19. A method according to claim 18, wherein the lipid is present in the formulation in a oncentration of about 20 millimolar.

20. A method according to claim 1, wherein the solubilizing agent is present in such a concentration in the range of about 5–70% by weight, based on the formulation, that the formulation, at room temperature, is substantially clear to the naked eye.

21. A method according to claim 20, wherein the solubilizing agent is present in a concentration of about 10–50% by weight, based on the formulation.

22. A method according to claim 1, wherein the water gelling agent used in the establishment of the hydrogel is selected from the group consisting of cellulose derivatives, polyacrylic acids, polymethacrylates, polyvinylpyrrolidones, polyvinyl alcohols and high molecular weight polyalkylene glycols.

23. A method according to claim 22, wherein the water gelling agent used in the establishment of the hydrogel is selected from the group consisting of carboxymethylcellulose and salts thereof, carbopol 934, povidone K30, and hydroxypropylmethylcellulose.

24. A method according to claim 1, wherein the formulation additionally contains a pharmaceutically acceptable non-ionic surfactant in such a concentration between about 0.01 and 2% by weight, calculated on the formulation, that it does not to any substantial extent impair the activity of the lipid.

25. A method according to claim 24, wherein the nonionic surfactant is a polysorbate.

26. A method according to claim 25, wherein the non-ionic surfactant is polyoxyethylene 20 sorbitan monolaurate.

27. A method according to claim 1, wherein the formulation contains a preservative which does not to any substantial extent impair the activity of the lipid.

28. A method according to claim 27, wherein the preservative is a mixture of methyl-p-hydroxy-benzoic acid and propyl-p-hydroxybenzoic acid, in the proportion of about 4:1 by weight.

29. A method according to claim 28, wherein the preservative mixture is present in the formulation in a concentration of about 0.05–0.2% by weight.

30. A method according to claim 1, wherein the formulation contains one or more antiviral agents in addition to the microbicidal lipid.

31. The method according to claim 1, wherein said mammal is a human.

32. A pharmaceutical formulation comprising a hydrogel which contains a) at least one microbicidal lipid as an active ingredient wherein the lipid is selected from the group consisting of $C_{6-18}$ fatty acids of salts thereof, $C_{6-18}$ fatty acid monoglyserides, $C_{6-18}$ fatty acid esters of monohydric alcohols, $C_{6-18}$ fatty alcohols, and $C_{6-18}$ fatty alcohols, and $C_{6-18}$ fatty alcohol monoglyceride ethers, the $C_{6-18}$ chain containing at least one double or triple bond when the number of carbon atoms there exceed 15, b) at least one water gelling agent selectd from the group consisting of polysaccharides, acrylic polymers, proteins and high molecular witht poyhydroxy compounds, and c) at least one solubilizing agent selected from the group consisting of lower polyhydric alcohol, polyalkylene glycols, and polyhydrosy ethers, which keeps the lipid dissolved in the hydrogel, the formulation being one which when incubated for 5 minutes with HSV-1 in a titer of 100 million $CCID_{50}$ per ml in Cell Culture Maintenance Medium in a concentration corresponding to 5 millimolar lipid will cause at least a thousand fold reduction of the virus titer, or which when incubated for 1 minute with HIV-1 in a titer of 10 million $CCID_{50}$ per ml in Cell Culture Maintenance Medium in a concentration corresponding to 20 millimolar lipid will cause at least a hundred fold reduction of the virus titer, or which when incubated for 10 minutes with C. trachomatis in a titer of 10 million IFU per ml in Cell Culture Maintenance Medium in a concentration corresponding to 5 millimolar lipid will cause at least a thousand fold reduction of the bacterial titer.

33. A pharmaceutical formulation according to claim 32, wherein the formulation is one which when incubated for 5 minutes with HSV-1 in a titer of 100 million $CCID_{50}$ per ml in Cell Culture Maintenance Medium in a concentration corresponding to 5 millimolar lipid will cause at least a ten thousand fold reduction of the virus titer, or which when incubated for 1 minute with HIV-1 in a titer of 10 million $CCID_{\_}$per ml in Cell Culture Maintenance Medium in a concentration corresponding to 20 millimolar lipid will cause at least a thousand fold reduction of the virus titer, or which when incubated for 10 minutes with C. trachomatis in a titer of 10 million IFU per ml in Cell Culture Maintenance Medium in a concentration corresponding to 5 millimolar lipid will cause at least a ten thousand fold reduction of the bacterial titer.

34. A pharmaceutical formulation according to claim 33, wherein the formulation is one which when incubated for 5 minutes with HSV-1 in a titer of 100 million $CCID_{50}$ per ml in Cell Culture Maintenance Medium in a concentration corresponding to 5 millimolar lipid will cause at least a hundred thousand fold reduction of the virus titer, or which when incubated for 1 minute with HIV-1 in a titer of 10 million $CCID_{50}$ per ml in Cell Culture Maintenance Medium in a concentration corresponding to 20 millimolar lipid will cause at least a ten thousand fold reduction of the virus titer, or which when incubated for 10 minutes with C. trachomatis in a titer of 10 million IFU per ml in Cell Culture Maintenance Medium in a concentration corresponding to 5 millimolar lipid will cause at least a hundred thousand fold reduction of the bacterial titer.

35. A pharmaceutical formulation according to claim 32, wherein the lipid is selected from the group consisting of $C_{6-14}$ fatty acids or salts thereof, $C_{6-14}$ fatty acid monoglycerides, $C_{6-14}$ fatty acid esters of monohydric alcohols, $C_{6-14}$ fatty alcohols, and $C_{6-14}$ fatty alcohol monoglyceride ethers.

36. A pharmaceutical formulation according to claim 35, wherein the fatty moieties are saturated.

37. A pharmaceutical formulation according to claim 32, wherein the lipid is selected from capric acid 1-monoglyceride, lauric acid and palmitoleic acid.

38. A pharmaceutical formulation according to claim 37, wherein the lipid is capric acid 1-monoglyceride.

39. A pharmaceutical formulation according to claim 32, wherein the solubilizing agent is a compound or compounds selected from the group consisting of the general formula IIIa $$R\text{—}(O\text{—}CH_2\text{—}CH_2)_q\text{—}OH \qquad (IIIa)$$

wherein q is an integer in the range from 1 to 5, R is H or $R_1CH_2$, and $R_1$ is a 5- or 6-membered aliphatic ring wherein from one to three carbon atoms may be replaced by nitrogen and/or oxygen atoms, said 5- or 6-membered ring optionally carrying from one to three substituents selected from the group consisting of halogen, amino, carboxy, and hydroxy.

40. A pharmaceutical formulation according to claim 39, wherein the solubilizing agent is a compound or compounds selected from the group consisting of compounds of the general formula IIIb

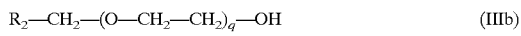

(IIIb)

wherein q is an integer in the range from 1 to 15, and $R_2$ designates a 5- or 6-membered aliphatic ring wherein from one to three carbon atoms may be replaced by nitrogen and/or oxygen atoms.

41. A pharmaceutical formulation according to claim 40, wherein the solubilizing agent is a compound or compounds selected from the group consisting of compounds of the general formula IIIc

(IIIc)

wherein q is an integer in the range from 1 to 15, and $R_3$ designates a 5- or 6-membered aliphatic ring wherein one or two carbon atoms may be replaced by oxygen atoms.

42. A pharmaceutical formulation according to claim 41, wherein the solubilizing agent is a compound or compounds selected from the group consisting of compounds of the general formula IIId

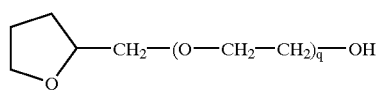

(IIId)

wherein q is an integer in the range from 1 to 15.

43. A pharmaceutical formulation according to claim 39, wherein q is an integer in the range from 1 to 8.

44. A pharmaceutical formulation according to claim 43, wherein q is an integer in the range from 1 to 4.

45. A pharmaceutical formulation according to claim 44, wherein the solubilizing agent is tetrahydrofurfuryl alcohol polyethylene glycol ether.

46. A pharmaceutical formulation according to claim 32, wherein the lipid is present in the formulation in a concentration of from about 1 to about 40 millimolar.

47. A pharmaceutical formulation according to claim 46, wherein the lipid is present in the formulation in a concentration of about 5–30 millimolar.

48. A pharmaceutical formulation according to claim 47, wherein the lipid is present in the formulation in a concentration of about 10–25 millimolar.

49. A pharmaceutical formulation according to claim 48, wherein the lipid is present in the formulation in a concentration of about 20 millimolar.

50. A pharmaceutical formulation according to claim 32, wherein the water gelling agent is selected from the group consisting of cellulose derivatives, polyacrylic acids, polymethacrylates, polyvinylpyrrolidones, polyvinyl alcohols and high molecular weight polyalkylene glycols.

51. A pharmaceutical formulation according to claim 50, wherein the water gelling agent is selected from the group consisting of carboxymethylcellulose and salts thereof, hydroxyproplmethylcellulose, carboxyvinylpolymer and polyvinylpyrrolidone.

52. A pharmaceutical formulation according to claim 32, wherein the solubilizing agent is present in a concentration in the range of about 5–70% by weight, based on the formulation, so that the formulation, at room temperature, is substantially clear to the naked eye.

53. A pharmaceutical formulation according to claim 52, wherein the solubilizing agent is present in a concentration of about 10–50% by weight, based on the formulation.

54. A pharmaceutical formulation according to claim 32, wherein the formulation additionally contains a pharmaceutically acceptable non-ionic surfactant in a concentration between about 0.01 and 2% by weight.

55. A pharmaceutical formulation according to claim 54, wherein the non-ionic surfactant is a polysorbate.

56. A pharmaceutical formulation according to claim 55, wherein the non-ionic surfactant is polyoxyethylene 20 sorbitan monolaurate.

57. A pharmaceutical formulation according to claim 32, wherein the formulation additionally contains a preservative.

58. A pharmaceutical formulation according to claim 57, wherein the preservative is a mixture of methyl-p-hydroxy-benzoic acid and propyl-p-hydroxy-benzoic acid, substantially in the proportion of 4:1 by weight.

59. A pharmaceutical formulation according to claim 58, wherein the preservative mixture is present in the formulation in a concentration of about 0.05–0.2% by weight.

60. A pharmaceutical formulation according to claim 32, wherein the formulation additionally contains one or more antiviral agents.

61. A pharmaceutical formulation comprising a) at least one microbicidal lipid as an active ingredient selected from the group consisting of $C_{6-14}$ fatty acids or salts thereof, $C_{6-14}$ fatty acid monoglycerides, $C_{6-14}$ fatty acid esters of monohydric alcohols, $C_{6-14}$ fatty alcohols, $C_{6-14}$ fatty alcohol monoglyceride ethers, unsaturated $C_{16}$ fatty acids or salts thereof, unsaturated $C_{16}$ fatty acid monoglycerides, unsaturated $C_{16}$ fatty acid esters of monohydric alcohols, unsaturated $C_{16}$ fatty alcohols, and unsaturated $C_{16}$ fatty alcohol monoglyceride ethers and b) a solubilizing agent selected from the group consisting of lower polyhydric alcohol, polyalkylene glycols and polyhydrosy ethers, which keeps the lipid dissolved in the formulation, the formulation being one which when incubated for 5 minutes with HSV-1 in a titer of 100 million $CCID_{50}$ per ml in Cell Culture Maintenance Medium in a concentration corresponding to 5 millimolar lipid will cause at least a thousand fold reduction of the virus titer, or which, when incubated for 1 minute with HIV-1 in a titer of 10 million $CCID_{50}$ per ml in Cell Culture Maintenance Medium in a concentration corresponding to 20 millimolar lipid will cause at least a hundred fold reduction of the virus titer, or which, when incubated for 10 minutes with C. trachomatis in a titer of 10 million IFU per ml in Cell Culture Maintenance Medium in a concentration corresponding to 5 millimolar lipid will cause at least a thousand fold reduction of the bacterial titer.

62. A pharmaceutical formulation according to claim 61, wherein the formulation further comprises a gel-forming agent.

63. A pharmaceutical formulation according to claim 62, wherein the formulation is in the form of a gel composition.

64. A pharmaceutical formulation according to claim 63, wherein the gel is a hydrogel.

65. A pharmaceutical formulation according to claim 61, wherein the fatty moieties are saturated.

66. A pharmaceutical formulation according to claim 61, wherein the formulation is one which when incubated for 5 minutes with HSV-1 in a titer of 100 million CCID$_{50}$ per ml in Cell Culture Maintenance Medium in a concentration corresponding to 5 millimolar lipid will cause at least a ten thousand fold reduction of the virus titer, or which, when incubated for 1 minute with HIV-1 in a titer of 10 million CCID$_{50}$ per ml in Cell Culture Maintenance Medium in a concentration corresponding to 20 millimolar lipid will cause at least a thousand fold reduction of the virus titer, or which, when incubated for 10 minutes with *C. trachomatis* in a titer of 10 million IFU per ml in Cell Culture Maintenance Medium in a concentration corresponding to 5 millimolar lipid will cause at least a ten thousand fold reduction of the bacterial titer.

67. A pharmaceutical formulation according to claim 66, wherein the formulation is one which when incubated for 5 minutes with HSV-1 in a titer of 100 million CCID$_{50}$ per ml in Cell Culture Maintenance Medium in a concentration corresponding to 5 millimolar lipid will cause at least a hundred thousand fold reduction of the virus titer, or which, when incubated for 1 minute with HIV-1 in a titer of 10 million CCID$_{50}$ per ml in Cell Culture Maintenance Medium in a concentration corresponding to 20 millimolar lipid will cause at least a ten thousand fold reduction of the virus titer, or which, when incubated for 10 minutes with *C. trachomatis* in a titer of 10 million IFU per ml in Cell Culture Maintenance Medium in a concentration corresponding to 5 millimolar lipid will cause at least a hundred thousand fold reduction of the bacterial titer.

68. A pharmaceutical formulation according to claim 61, wherein the lipid is selected from lauric acid and palmitoleic acid.

69. A pharmaceutical formulation according to claim 61, wherein the lipid is capric acid 1-monoglyceride.

70. A pharmaceutical formulation according to claim 61, wherein the solubilizing agent is a compound or compounds selected from the group consisting of compounds of the general formula I:

wherein n is an integer in the range from 1 to 4, m is an integer in the range from 1 to 15, and R is H or R$_1$CH$_2$,
  wherein R$_1$ designates a 5- or 6-membered aliphatic ring wherein from one to three carbon atoms may be replaced by nitrogen and/or oxygen atoms, said 5- or 6-membered ring optionally carrying from one to three substituents selected from the group consisting of halogen, amino, carboxy, and hydroxy;

and compounds of the general formula II:

wherein k is an integer in the range from 1 to 15, and
R is H or R$_1$CH$_2$,
  wherein R$_1$ is as defined above.

71. A pharmaceutical formulation according to claim 70, wherein n is 2 or 3, and R is H or R$_2$CH$_2$,
  wherein R$_2$ designates a 5- or 6-membered aliphatic ring wherein from one to three carbon atoms may be replaced by nitrogen and/or oxygen atoms.

72. A pharmaceutical formulation according to claim 71, wherein n is 2, and
R is H or R$_3$CH$_2$,
wherein R$_3$ designates a 5- or 6-membered aliphatic ring wherein one or two carbon atoms may be replaced by oxygen atoms.

73. A pharmaceutical formulation according to claim 72, wherein
R is H or

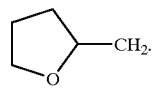

74. A pharmaceutical formulation according to claim 70, wherein m is an integer in the range from 1 to 8.

75. A pharmaceutical formulation according to claim 74, wherein the solubilizing agent is a compound or compounds selected from the group consisting of compounds of the general formula I

wherein m is an integer in the range from 1 to 4, and
R is H or

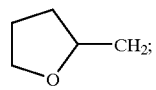

and compounds of the general formula (II)

wherein k is an integer in the range from 1 to 4.

76. A pharmaceutical formulation according to claim 75, wherein m is 1 or 2, and k is 1 or 2.

77. A pharmaceutical formulation according to claim 75, wherein the solubilizing agent is selected from the group consisting of tetrahydrofurfuryl alcohol polyethylene glycol ether, ethylene glycol and propylene glycol, and mixtures thereof.

78. A pharmaceutical formulation according to claim 77, wherein the solubilizing agent is tetrahydrofurfuryl alcohol polyethylene glycol ether.

79. A pharmaceutical formulation according to claim 61, wherein the lipid is present in the formulation in a concentration of from about 1 to about 40 millimolar.

80. A pharmaceutical formulation according to claim 79, wherein the lipid is present in the formulation in a concentration of about 5–30 millimolar.

81. A pharmaceutical formulation according to claim 80, wherein the lipid is present in the formulation in a concentration of about 10–25 millimolar.

82. A pharmaceutical formulation according to claim 81, wherein the lipid is present in the formulation in a concentration of about 20 millimolar.

83. A pharmaceutical formulation according to claim 61, wherein the solubilizing agent is present in a concentration in the range of about 5–70% by weight, based on the formulation, so that the formulation, at room temperature, is substantially clear to the naked eye.

84. A pharmaceutical formulation according to claim 83, wherein the solubilizing agent is present in a concentration of about 10–50% by weight, based on the formulation.

85. A pharmaceutical composition according to claim 64, wherein the hydrogel is established by means of a water gelling agent selected from the group consisting of polysaccharides, acrylic polymers, proteins and high molecular weight polyhydroxy compounds.

86. A pharmaceutical formulation according to claim 85, wherein the water gelling agent used in the establishment of the hydrogel is selected from the group consisting of cellulose derivatives, polyacrylic acids, polymethacrylates, polyvinylpyrrolidones, polyvinyl alcohols and high molecular weight polyalkylene glycols.

87. A pharmaceutical formulation according to claim 86, wherein the water gelling agent used in the establishment of the hydrogel is selected from the group consisting of carboxymethylcellulose and salts thereof, carboxyvinyl polymer, polyvinyl pyrrolidone, and hydroxypropylmethylcellulose.

88. A pharmaceutical formulation according to claim 61, wherein the formulation additionally contains a pharmaceutically acceptable non-ionic surfactant in a concentration between about 0.01 and 2% by weight, calculated on the formulation, so that it does not to any substantial extent impair the activity of the lipid.

89. A pharmaceutical formulation according to claim 88, wherein the non-ionic surfactant is a polysorbate.

90. A pharmaceutical formulation according to claim 89, wherein the non-ionic surfactant is polyoxyethylene 20 sorbitan monolaurate.

91. A pharmaceutical formulation according to claim 61, wherein the formulation contains a preservative which does not substantially impair the activity of the lipid.

92. A pharmaceutical formulation according to claim 91, wherein the preservative is a mixture of methyl-p-hydroxy-benzoic acid and propyl-p-hydroxy-benzoic acid, substantially in the proportion of 4:1 by weight.

93. A pharmaceutical formulation according to claim 92, wherein the preservative mixture is present in the formulation in a concentration of about 0.05–0.2% by weight.

94. A pharmaceutical formulation according to claim 61, wherein the formulation additionally contains one or more antiviral agents.

95. A method for treating infections caused by bacteria, fungi or virus in skin or mucosal membranes, comprising topically administering an effective amount of a formulation which contains a) at least one microbicidal lipid as an active ingredient, wherein the lipid is selected from the group consisting of $C_{6-18}$ fatty acids or salts thereof $C_{6-18}$ fatty acid monoglycerides, $C_{6-18}$ fatty acid esters of monohydric alcohols, $C_{6-18}$ fatty alcohols, and $C_{6-18}$ fatty alcohol monoglyceride ethers, the $C_{6-18}$ chain containing at least one double or triple bond when the number of carbon atoms thereof exceeds 15 and b) at least one solubilizing agent selected from the group consisting of lower polyhydric alcohols, polyalkylene glycols, and polyhydroxy ethers, which solubilizing agent keeps the lipid dissolved in the formulation, and the formulation being one which when incubated for 5 minutes with HSV-1 in a titer of 100 million $CCID_{50}$ per ml in Cell Culture Maintenance Medium in a concentration corresponding to 5 millimolar lipid will cause at least a thousand fold reduction of the virus titer, or which, when incubated for 1 minute with HIV-1 in a titer of 10 million $CCID_{50}$ per ml in Cell Culture Maintenance Medium in a concentration corresponding to 20 millimolar lipid will cause at least a hundred fold reduction of the virus titer, or which, when incubated for 10 minutes with *C. trachomatis* in a titer of 10 million IFU per ml in Cell Culture Maintenance Medium in a concentration corresponding to 5 millimolar lipid will cause at least a thousand fold reduction of the bacterial titer.

96. The method according to claim 95, for preventing or treating infections in oral or anal mucosa membranes.

* * * * *